United States Patent
Wicks et al.

(10) Patent No.: US 7,878,553 B2
(45) Date of Patent: Feb. 1, 2011

(54) RELEASABLE CONNECTION ASSEMBLY FOR JOINING TUBING SECTIONS

(75) Inventors: Jeffrey Clark Wicks, Fort Collins, CO (US); Bruce Alan Williams, Fort Collins, CO (US)

(73) Assignee: Value Plastics, Inc., Fort Collins, CO (US)

( * ) Notice: Subject to any disclaimer, the term of this patent is extended or adjusted under 35 U.S.C. 154(b) by 0 days.

(21) Appl. No.: 12/430,745

(22) Filed: Apr. 27, 2009

(65) Prior Publication Data

US 2009/0256355 A1 Oct. 15, 2009

Related U.S. Application Data

(63) Continuation of application No. 10/940,313, filed on Sep. 13, 2004, now abandoned.

(60) Provisional application No. 60/502,325, filed on Sep. 12, 2003.

(51) Int. Cl.
*F16L 39/00* (2006.01)

(52) U.S. Cl. .................. 285/319; 285/272; 285/275; 285/305; 285/921

(58) Field of Classification Search ............. 285/272, 285/275, 305, 307, 319, 331, 921; 403/329, 403/DIG. 14
See application file for complete search history.

(56) References Cited

U.S. PATENT DOCUMENTS

| | | |
|---|---|---|
| 163,261 A | 5/1875 | Ruppenthal |
| 185,896 A | 1/1877 | Curtis |
| 187,982 A | 3/1877 | Pirsson et al. |
| 200,944 A | 3/1878 | Smith |
| 235,580 A | 12/1880 | Smith et al. |
| 327,509 A | 10/1885 | Aldridge |
| 584,008 A | 6/1887 | Munson |
| 465,868 A | 12/1891 | List |
| 725,421 A | 4/1903 | Dinkins |
| 727,982 A | 5/1903 | Ludwig |
| 874,957 A | 12/1907 | Godley |
| 884,461 A | 4/1908 | Browne |
| 909,131 A | 1/1909 | Antic |
| 951,889 A | 3/1910 | Teuer |
| 1,029,819 A | 6/1912 | Nylander |

(Continued)

FOREIGN PATENT DOCUMENTS

WO WO2006/135666 12/2006

OTHER PUBLICATIONS

Brochure, "Precision Components", Value Plastics, Inc., 2002.

(Continued)

*Primary Examiner*—James M Hewitt
*Assistant Examiner*—Jay R Ripley
(74) *Attorney, Agent, or Firm*—Dorsey & Whitney LLP

(57) ABSTRACT

A connection assembly for creating a releasable fluid seal connection between two or more sections of tubing includes a male fitting and a female fitting. Connection assemblies generally include the male fitting having a pair of clasps that releasably interact with corresponding catch structures on the female fitting. Interactions between the female and male fittings can be rotatable with respect to the male and/or female fittings. Buckle structures are also disclosed having connection capabilities for a plurality of sections of tubing.

7 Claims, 21 Drawing Sheets

U.S. PATENT DOCUMENTS

| | | |
|---|---|---|
| 1,033,187 A | 7/1912 | Metzger |
| 1,039,354 A | 9/1912 | Bonadio |
| 1,077,417 A | 11/1913 | McCracken |
| 1,078,112 A | 11/1913 | Storm |
| 1,193,446 A | 8/1916 | Wells |
| 1,239,345 A | 9/1917 | Brown |
| 1,255,847 A | 2/1918 | Arkin |
| 1,259,684 A | 3/1918 | Vinten |
| 1,489,310 A | 4/1924 | Critchlow |
| 1,526,218 A | 2/1925 | Johnson |
| 1,578,504 A | 3/1926 | Bronson et al. |
| 1,587,079 A | 6/1926 | Machino |
| 1,767,073 A | 6/1930 | Ingold |
| 1,863,360 A | 6/1932 | Weatherhead |
| 1,950,947 A | 3/1934 | Mulroyan |
| 2,023,428 A | 12/1935 | Liebhardt |
| 2,056,524 A | 10/1936 | Johnson |
| 2,066,473 A | 1/1937 | Jorgensen |
| 2,097,628 A | 11/1937 | Liebhardt |
| 2,099,335 A | 11/1937 | Hansen |
| 2,108,714 A | 2/1938 | Hirsch et al |
| 2,139,745 A | 12/1938 | Goodall |
| 2,147,355 A | 2/1939 | Scholtes |
| 2,159,116 A | 5/1939 | Zacharias |
| 2,211,147 A | 8/1940 | Miller |
| 2,257,321 A | 9/1941 | Arnold |
| 2,263,293 A | 11/1941 | Ewald |
| 2,340,119 A | 1/1944 | Graham |
| 2,346,445 A | 4/1944 | Merker et al. |
| 2,352,728 A | 7/1944 | Merker et al. |
| 2,429,782 A | 10/1947 | Versoy |
| 2,432,946 A | 12/1947 | Theunissen |
| 2,470,800 A | 5/1949 | Ashton |
| 2,479,499 A | 8/1949 | Le Clair |
| 2,500,720 A | 3/1950 | Van der Heem |
| 2,507,536 A | 5/1950 | Goodson |
| 2,516,583 A | 7/1950 | Moore |
| 2,535,740 A | 12/1950 | Knopp |
| 2,577,009 A | 12/1951 | Frantz |
| 2,626,974 A | 1/1953 | Howard et al. |
| 2,630,131 A | 3/1953 | Snyder |
| 2,661,018 A | 12/1953 | Snyder |
| 2,701,147 A | 2/1955 | Summerville |
| 2,722,399 A | 11/1955 | Oetiker |
| 2,753,195 A | 7/1956 | Palmer |
| 2,774,616 A | 12/1956 | Dodd et al. |
| 2,790,571 A | 4/1957 | Flaith et al. |
| 2,864,628 A | 12/1958 | Edleson |
| 2,915,325 A | 12/1959 | Foster |
| 2,926,934 A | 3/1960 | Gill |
| 2,931,668 A | 4/1960 | Baley |
| 2,937,892 A | 5/1960 | Prescott, Jr. |
| 2,948,553 A | 8/1960 | Gill et al. |
| 2,991,090 A | 7/1961 | De Cenzo |
| 3,017,203 A | 1/1962 | Macleod |
| 3,037,497 A | 6/1962 | Roberson |
| 3,073,342 A | 1/1963 | Magorien |
| 3,078,068 A | 2/1963 | Romney |
| D196,473 S | 10/1963 | Hill |
| 3,124,157 A | 3/1964 | Krzewina |
| 3,171,196 A | 3/1965 | Helitas |
| 3,217,771 A | 11/1965 | Beall et al. |
| 3,227,380 A | 1/1966 | Pinkston |
| 3,237,974 A | 3/1966 | Press |
| 3,245,703 A | 4/1966 | Manly |
| 3,276,799 A | 10/1966 | Moore et al. |
| 3,279,497 A | 10/1966 | Norton et al |
| 3,314,696 A | 4/1967 | Ferguson et al. |
| D209,166 S | 11/1967 | Hunt |
| D209,168 S | 11/1967 | Hunt |
| 3,352,576 A | 11/1967 | Thorne-Thomsen |
| 3,382,892 A | 5/1968 | Cerbin |
| 3,403,930 A | 10/1968 | Bernier |
| 3,448,760 A | 6/1969 | Cranage |
| 3,450,424 A | 6/1969 | Calisher |
| 3,512,808 A | 5/1970 | Graham |
| 3,523,701 A | 8/1970 | Graham |
| 3,538,940 A | 11/1970 | Graham |
| 3,542,338 A | 11/1970 | Scaramucci |
| 3,545,490 A | 12/1970 | Burrus |
| 3,550,626 A | 12/1970 | Daniels et al. |
| 3,560,027 A | 2/1971 | Graham |
| 3,563,265 A | 2/1971 | Graham |
| 3,574,314 A | 4/1971 | Quercia |
| 3,588,149 A | 6/1971 | Demler |
| 3,596,933 A | 8/1971 | Luckenbill |
| 3,599,843 A | 8/1971 | Johnston |
| 3,600,917 A | 8/1971 | Krock |
| 3,690,336 A | 9/1972 | Drum |
| 3,712,583 A | 1/1973 | Martindale et al. |
| 3,750,238 A | 8/1973 | Tanner |
| 3,815,887 A | 6/1974 | Curtis et al. |
| 3,817,561 A | 6/1974 | Kay |
| 3,876,234 A | 4/1975 | Harms |
| 3,889,710 A | 6/1975 | Brost |
| 3,899,200 A | 8/1975 | Gamble |
| 3,921,656 A | 11/1975 | Meisenheimer, Jr. et al. |
| 3,979,934 A | 9/1976 | Isenmann |
| 3,990,674 A | 11/1976 | Schattenberg |
| 4,025,049 A | 5/1977 | Schmidt |
| 4,039,213 A | 8/1977 | Walters |
| 4,072,330 A | 2/1978 | Brysch |
| 4,099,748 A | 7/1978 | Kavick |
| 4,129,145 A | 12/1978 | Wynn |
| 4,142,546 A | 3/1979 | Sandau |
| D252,470 S | 7/1979 | Pawlak |
| 4,181,149 A | 1/1980 | Cox |
| D254,505 S | 3/1980 | Parsons et al. |
| D255,145 S | 5/1980 | Nederman |
| 4,220,360 A | 9/1980 | Jacek et al. |
| D258,526 S | 3/1981 | Nederman |
| D259,278 S | 5/1981 | McCaw |
| 4,271,865 A | 6/1981 | Galloway et al. |
| 4,287,644 A | 9/1981 | Durand |
| 4,296,949 A | 10/1981 | Muetterties et al. |
| 4,319,774 A | 3/1982 | Kavick |
| 4,330,010 A | 5/1982 | Drescher et al. |
| 4,330,142 A | 5/1982 | Paini |
| 4,331,175 A | 5/1982 | Brake et al. |
| 4,331,177 A | 5/1982 | Makishima |
| 4,340,200 A | 7/1982 | Stegmeier |
| 4,345,786 A | 8/1982 | Egert |
| 4,346,703 A | 8/1982 | Dennehey |
| 4,351,351 A | 9/1982 | Flory et al. |
| 4,366,816 A | 1/1983 | Bayard et al. |
| 4,393,548 A | 7/1983 | Herb |
| 4,397,442 A | 8/1983 | Larkin |
| 4,434,121 A | 2/1984 | Schaper |
| 4,436,125 A | 3/1984 | Blenkush |
| 4,437,689 A | 3/1984 | Goebel et al. |
| 4,439,188 A | 3/1984 | Dennehey |
| 4,458,719 A | 7/1984 | Strybel |
| 4,500,118 A | 2/1985 | Blenkush |
| 4,527,745 A | 7/1985 | Butterfield et al. |
| 4,541,457 A | 9/1985 | Blenkush |
| 4,541,657 A | 9/1985 | Smyth |
| D282,962 S | 3/1986 | Gerber |
| 4,603,888 A | 8/1986 | Goodall et al. |
| 4,613,112 A | 9/1986 | Phlipot et al. |
| 4,616,859 A | 10/1986 | Brunet |
| 4,632,436 A | 12/1986 | Kimura |
| 4,658,326 A | 4/1987 | Clark et al. |
| 4,694,544 A | 9/1987 | Chapman |
| 4,699,298 A | 10/1987 | Grant et al. |

| | | | | | | |
|---|---|---|---|---|---|---|
| 4,703,957 | A | 11/1987 | Blenkush | D380,262 | S | 6/1997 | Van Funderburk et al. |
| 4,706,847 | A | 11/1987 | Sankey et al. | D387,147 | S | 12/1997 | Vandermast et al. |
| 4,712,280 | A | 12/1987 | Fildan | 5,695,223 | A | 12/1997 | Boticki |
| 4,738,401 | A | 4/1988 | Filicicchia | D388,876 | S | 1/1998 | Sampson |
| 4,753,268 | A | 6/1988 | Palau | 5,709,244 | A | 1/1998 | Patriquin et al. |
| 4,776,067 | A | 10/1988 | Sorensen | 5,725,258 | A | 3/1998 | Kujawski |
| 4,790,567 | A | 12/1988 | Kawano et al. | 5,737,810 | A | 4/1998 | Krauss |
| 4,790,569 | A | 12/1988 | Chaffee | 5,745,957 | A | 5/1998 | Khokhar et al. |
| 4,792,115 | A | 12/1988 | Jindra et al. | 5,746,414 | A | 5/1998 | Weldon et al. |
| 4,793,637 | A | 12/1988 | Laipply et al. | 5,762,646 | A | 6/1998 | Cotter |
| D300,361 | S | 3/1989 | Tokarz | 5,799,987 | A | 9/1998 | Sampson |
| 4,827,921 | A | 5/1989 | Rugheimer | 5,820,614 | A | 10/1998 | Erskine et al. |
| 4,832,237 | A | 5/1989 | Hurford, Jr. | 5,845,943 | A | 12/1998 | Ramacier, Jr. et al. |
| 4,834,423 | A | 5/1989 | DeLand | 5,855,568 | A | 1/1999 | Battiato et al. |
| 4,844,512 | A | 7/1989 | Gahwiler | 5,882,047 | A | 3/1999 | Ostrander et al. |
| 4,863,201 | A | 9/1989 | Carstens | D407,803 | S | 4/1999 | Redman |
| 4,896,402 | A | 1/1990 | Jansen et al. | 5,897,142 | A * | 4/1999 | Kulevsky .................... 285/308 |
| 4,900,065 | A | 2/1990 | Houck | 5,911,367 | A | 6/1999 | McInerney |
| 4,903,995 | A | 2/1990 | Blenkush et al. | 5,911,403 | A | 6/1999 | deCler et al. |
| 4,923,228 | A | 5/1990 | Laipply et al. | 5,911,404 | A | 6/1999 | Cheng |
| 4,934,655 | A | 6/1990 | Blenkush et al. | 5,930,424 | A | 7/1999 | Heimberger et al. |
| 4,935,992 | A | 6/1990 | Due | 5,938,244 | A | 8/1999 | Meyer |
| 4,949,745 | A | 8/1990 | McKeon | 5,941,577 | A | 8/1999 | Musellec |
| 4,969,879 | A | 11/1990 | Lichte | D413,967 | S | 9/1999 | Yuen |
| D313,067 | S | 12/1990 | Kotake et al. | 5,957,898 | A | 9/1999 | Jepson et al. |
| D313,277 | S | 12/1990 | Haining | 5,964,485 | A | 10/1999 | Hame et al. |
| D314,050 | S | 1/1991 | Sone | 5,975,489 | A | 11/1999 | deCler et al. |
| D314,233 | S | 1/1991 | Medvick | 5,984,378 | A | 11/1999 | Ostrander et al. |
| 4,982,736 | A | 1/1991 | Schneider | 6,015,171 | A | 1/2000 | Schorn |
| 4,991,880 | A | 2/1991 | Bernart | D419,861 | S | 2/2000 | Khokhar |
| 5,009,252 | A | 4/1991 | Faughn | 6,024,124 | A | 2/2000 | Braun et al. |
| 5,033,777 | A | 7/1991 | Blenkush | 6,029,701 | A | 2/2000 | Chaffardon et al. |
| 5,052,725 | A | 10/1991 | Meyer et al. | 6,032,691 | A | 3/2000 | Powell et al. |
| 5,074,601 | A | 12/1991 | Spors et al. | D422,487 | S | 4/2000 | Khokhar |
| 5,076,615 | A | 12/1991 | Sampson | 6,050,297 | A | 4/2000 | Ostrowski et al. |
| 5,078,429 | A | 1/1992 | Braut et al. | 6,076,234 | A | 6/2000 | Khokhar et al. |
| 5,090,448 | A | 2/1992 | Truchet | 6,077,259 | A | 6/2000 | Caizza et al. |
| 5,090,747 | A | 2/1992 | Kotake | 6,082,401 | A | 7/2000 | Braun et al. |
| 5,094,482 | A | 3/1992 | Petty et al. | 6,089,540 | A | 7/2000 | Heinrichs et al. |
| 5,104,158 | A | 4/1992 | Meyer et al. | 6,112,855 | A | 9/2000 | Camacho et al. |
| D326,155 | S | 5/1992 | Boehringer et al. | 6,123,690 | A | 9/2000 | Mejslov |
| 5,112,084 | A | 5/1992 | Washizu | 6,135,150 | A | 10/2000 | Powell et al. |
| 5,114,250 | A | 5/1992 | Usui | 6,135,992 | A | 10/2000 | Wang |
| 5,123,677 | A | 6/1992 | Kreczko et al. | 6,152,914 | A | 11/2000 | Van De Kerkhof et al. |
| 5,160,177 | A | 11/1992 | Washizu | 6,161,578 | A | 12/2000 | Braun et al. |
| 5,165,733 | A | 11/1992 | Sampson | 6,182,694 | B1 | 2/2001 | Sievers et al. |
| 5,176,406 | A | 1/1993 | Straghan | 6,189,560 | B1 | 2/2001 | Reynolds |
| D333,178 | S | 2/1993 | Novy | 6,199,919 | B1 | 3/2001 | Kawasaki et al. |
| 5,190,224 | A | 3/1993 | Hamilton | 6,221,064 | B1 | 4/2001 | Nadal |
| 5,222,279 | A | 6/1993 | Frano et al. | 6,231,089 | B1 | 5/2001 | DeCler et al. |
| 5,228,724 | A | 7/1993 | Godeau | D444,054 | S | 6/2001 | Bernard et al. |
| 5,232,020 | A | 8/1993 | Mason et al. | 6,257,626 | B1 | 7/2001 | Campau |
| D339,417 | S | 9/1993 | Sampson et al. | 6,261,282 | B1 | 7/2001 | Jepson et al. |
| 5,316,041 | A | 5/1994 | Ramacier, Jr. et al. | 6,293,596 | B1 | 9/2001 | Kinder |
| 5,330,235 | A | 7/1994 | Wagner et al. | 6,302,147 | B1 | 10/2001 | Rose et al. |
| 5,356,183 | A | 10/1994 | Cole | 6,318,764 | B1 | 11/2001 | Trede et al. |
| 5,374,088 | A | 12/1994 | Moretti et al. | 6,344,033 | B1 | 2/2002 | Jepson et al. |
| 5,385,311 | A | 1/1995 | Morikawa et al. | D459,206 | S | 6/2002 | Caveney et al. |
| 5,385,331 | A | 1/1995 | Allread et al. | 6,402,207 | B1 | 6/2002 | Segal et al. |
| D357,307 | S | 4/1995 | Ramacier, Jr. et al. | 6,423,053 | B1 | 7/2002 | Lee |
| 5,405,339 | A | 4/1995 | Kohnen et al. | 6,481,759 | B1 | 11/2002 | Kawasaki et al. |
| 5,405,340 | A | 4/1995 | Fageol et al. | 6,485,483 | B1 | 11/2002 | Fujii |
| 5,437,650 | A | 8/1995 | Larkin et al. | 6,505,866 | B1 | 1/2003 | Nakamura et al. |
| 5,494,074 | A | 2/1996 | Ramacier, Jr. et al. | 6,520,546 | B2 | 2/2003 | Szabo |
| 5,507,733 | A | 4/1996 | Larkin et al. | D471,261 | S | 3/2003 | Kozu |
| D372,093 | S | 7/1996 | Sampson et al. | 6,540,263 | B1 | 4/2003 | Sausner |
| 5,536,258 | A | 7/1996 | Folden | 6,595,964 | B2 | 7/2003 | Finley et al. |
| 5,547,166 | A | 8/1996 | Engdahl | 6,612,634 | B1 | 9/2003 | Zoppas |
| 5,553,895 | A | 9/1996 | Karl et al. | 6,626,465 | B2 | 9/2003 | Lacroix et al. |
| D375,160 | S | 10/1996 | Sampson et al. | D481,125 | S | 10/2003 | Hayamizu |
| 5,568,946 | A | 10/1996 | Jackowski | 6,641,177 | B1 | 11/2003 | Pinciaro |
| 5,595,217 | A | 1/1997 | Gillen et al. | 6,649,829 | B2 | 11/2003 | Garber et al. |
| 5,628,726 | A | 5/1997 | Cotter | 6,652,007 | B1 | 11/2003 | Hwang |

| | | |
|---|---|---|
| 6,669,681 B2 | 12/2003 | Jepson et al. |
| 6,676,172 B2 | 1/2004 | Alksnis |
| 6,688,654 B2 | 2/2004 | Romero |
| 6,692,038 B2 | 2/2004 | Braun |
| 6,722,705 B2 | 4/2004 | Korkor |
| 6,783,520 B1 | 8/2004 | Candray et al. |
| D497,428 S | 10/2004 | Hayamizu |
| 6,799,747 B1 | 10/2004 | Lai |
| D498,533 S | 11/2004 | Hayamizu |
| 6,840,277 B1 | 1/2005 | Nimberger |
| 6,848,723 B2 | 2/2005 | Lamich |
| 6,871,878 B2 | 3/2005 | Miros |
| D503,778 S | 4/2005 | Wicks |
| 6,886,803 B2 | 5/2005 | Mikiya et al. |
| 6,897,374 B2 | 5/2005 | Garber et al. |
| 6,899,315 B2 | 5/2005 | Maiville et al. |
| D507,647 S | 7/2005 | Beck et al. |
| 6,929,246 B2 | 8/2005 | Arzenton et al. |
| 6,945,273 B2 | 9/2005 | Reid |
| 6,949,084 B2 | 9/2005 | Marggi et al. |
| 6,997,919 B2 | 2/2006 | Olsen et al. |
| 7,005,581 B2 | 2/2006 | Burnette |
| 7,011,342 B2 | 3/2006 | Guivarc'h et al. |
| D522,109 S | 5/2006 | White et al. |
| 7,044,161 B2 | 5/2006 | Tiberghien |
| 7,044,506 B2 | 5/2006 | Dong |
| D523,553 S | 6/2006 | Beck et al. |
| 7,108,297 B2 | 9/2006 | Takayanagi et al. |
| 7,128,348 B2 | 10/2006 | Kawamura et al. |
| 7,137,654 B2 | 11/2006 | Segal et al. |
| 7,147,252 B2 | 12/2006 | Teuscher et al. |
| 7,153,296 B2 | 12/2006 | Mitchell |
| D550,355 S | 9/2007 | Racz et al. |
| D569,955 S | 5/2008 | Chen |
| D570,457 S | 6/2008 | Brown |
| 7,390,029 B2 | 6/2008 | Matsubara |
| 7,677,608 B2 | 3/2010 | Takayanagi |
| 2001/0054819 A1 | 12/2001 | Guest |
| 2002/0156344 A1 | 10/2002 | Pasricha et al. |
| 2004/0232696 A1 | 11/2004 | Andre |
| 2005/0001425 A1 | 1/2005 | deCler et al. |
| 2005/0012330 A1 | 1/2005 | Schmidt |
| 2005/0057042 A1 | 3/2005 | Wicks |
| 2005/0082828 A1 | 4/2005 | Wicks et al. |
| 2005/0211934 A1 | 9/2005 | Garber et al. |
| 2005/0258646 A1 | 11/2005 | Gunderson |
| 2007/0029796 A1 | 2/2007 | Bibby |
| 2007/0169825 A1 | 7/2007 | Packham et al. |
| 2007/0209716 A1 | 9/2007 | Rankin |
| 2008/0061553 A1 | 3/2008 | Schmidt |
| 2008/0200901 A1 | 8/2008 | Rasmussen et al. |
| 2008/0277924 A1 | 11/2008 | Jensen et al. |
| 2010/0001516 A1 | 1/2010 | Pisula, Jr. et al. |
| 2010/0056975 A1 | 3/2010 | Dale et al. |

OTHER PUBLICATIONS

U.S. Appl. No. 29/297,829, filed Nov. 19, 2007, Lombardi et al., Pending.
U.S. Appl. No. 29/339,063, filed Jun. 23, 2009, Wicks et al., Pending.
U.S. Appl. No. 29/341,451, filed Aug. 5, 2009, Williams et al., Pending.
U.S. Appl. No. 29/351,665, filed Dec. 9, 2009, Lewis et al., Pending.
U.S. Appl. No. 29/352,637, filed Dec. 23, 2009, Lewis, Pending.
U.S. Appl. No. 29/353,314, filed Jan. 6, 2010, Lombardi, III et al., Pending.
U.S. Appl. No. 29/353,317, filed Jan. 6, 2010, Lombardi, III et al., Pending.
U.S. Appl. No. 29/353,318, filed Jan. 6, 2010, Lombardi, III et al., Pending.

* cited by examiner

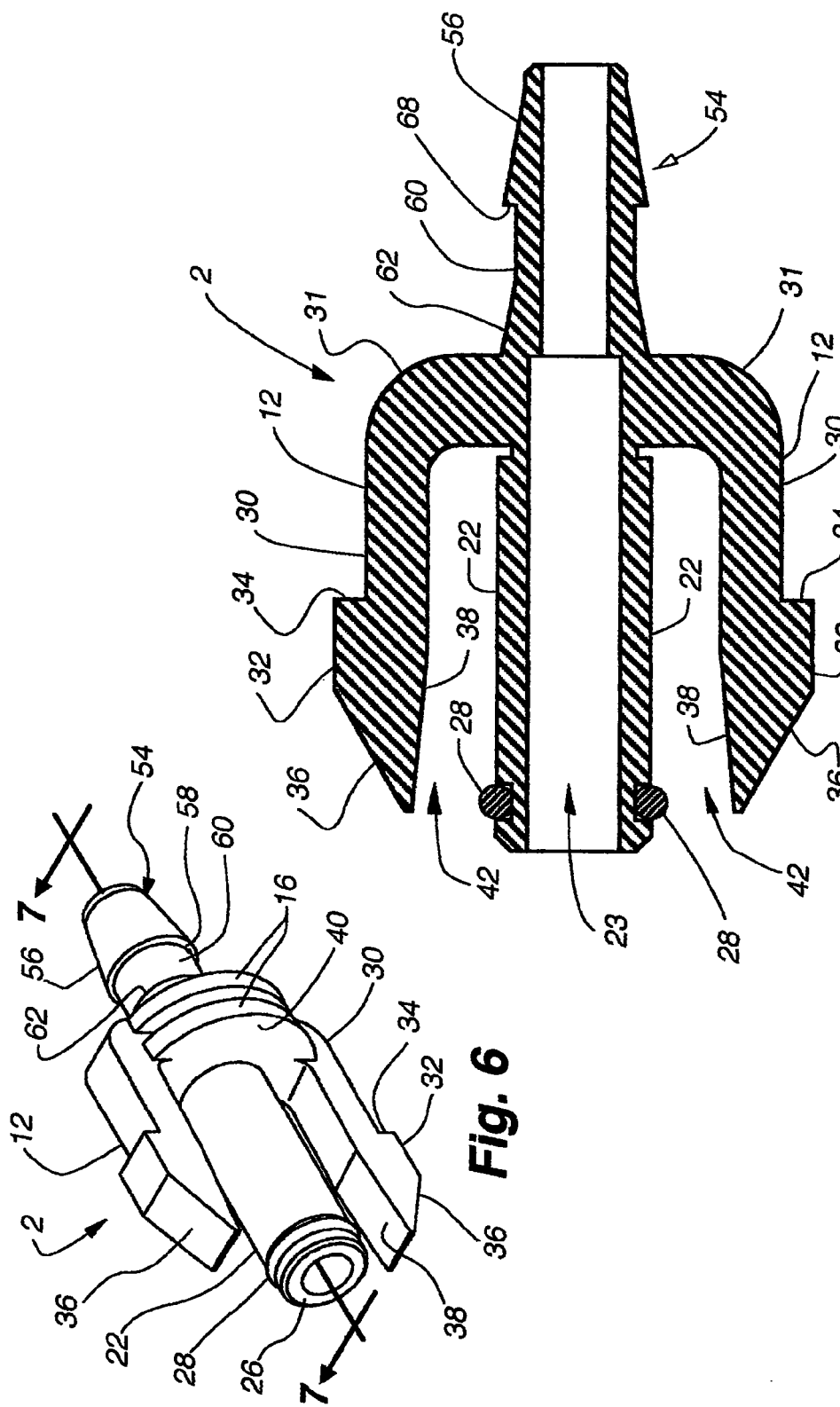

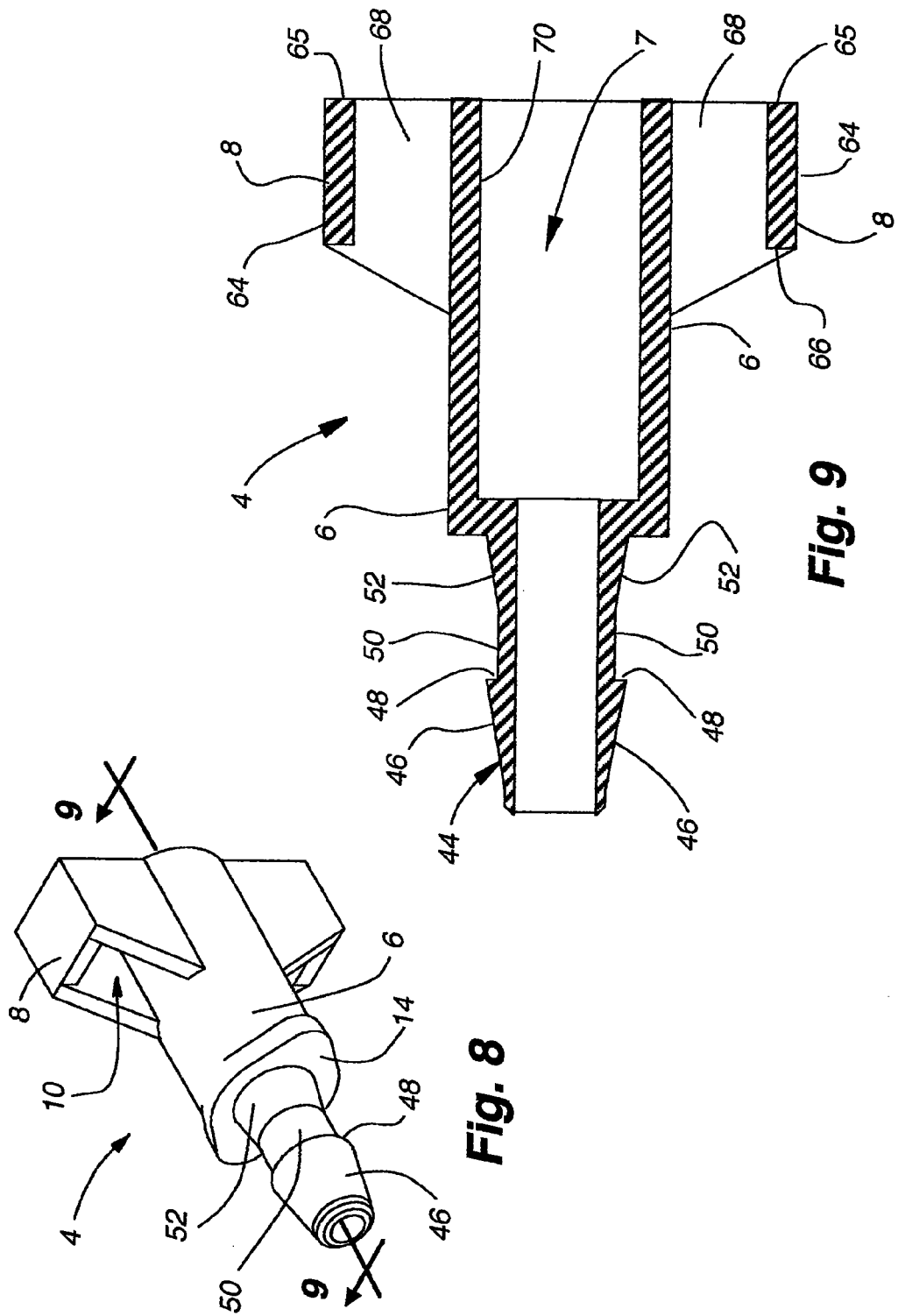

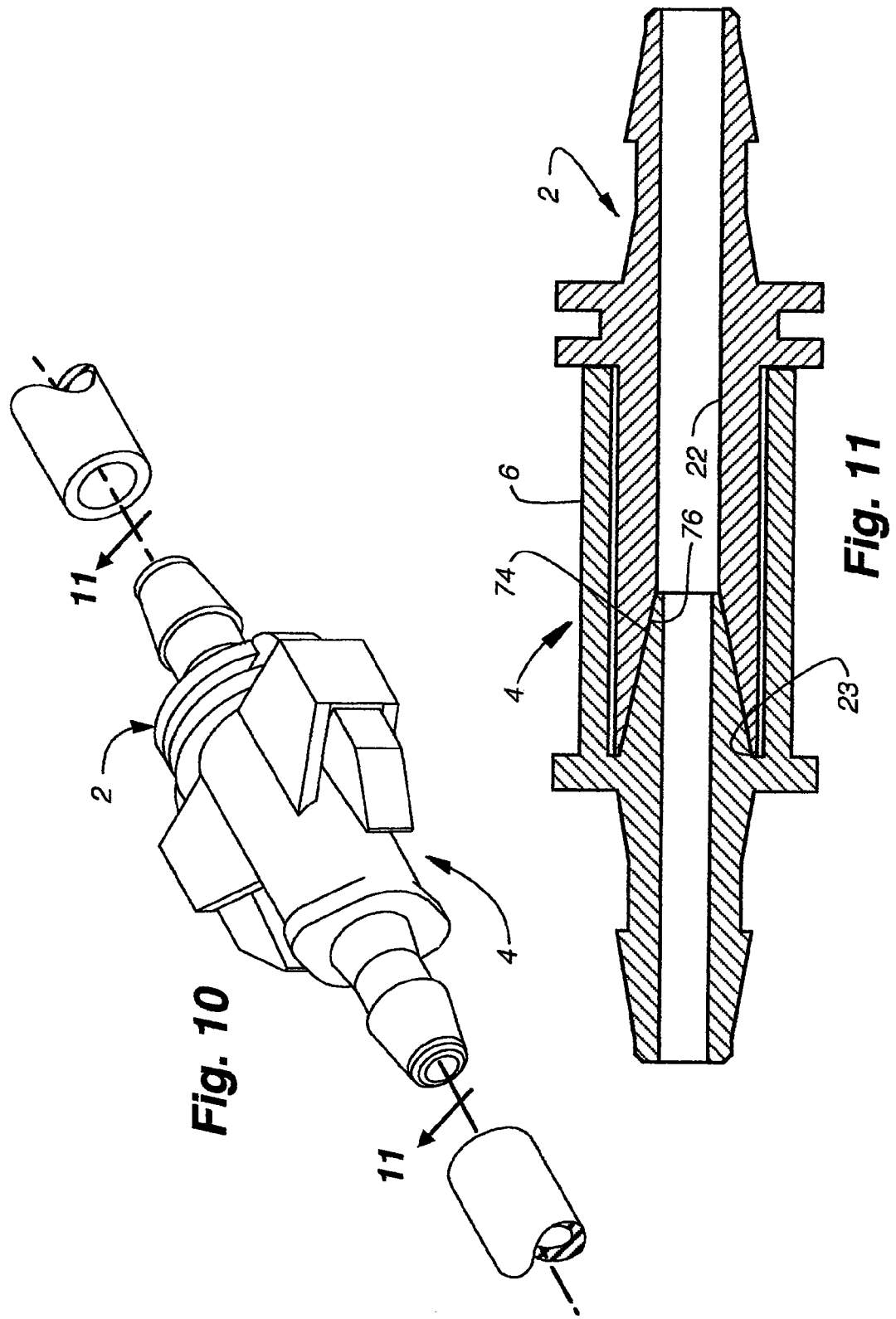

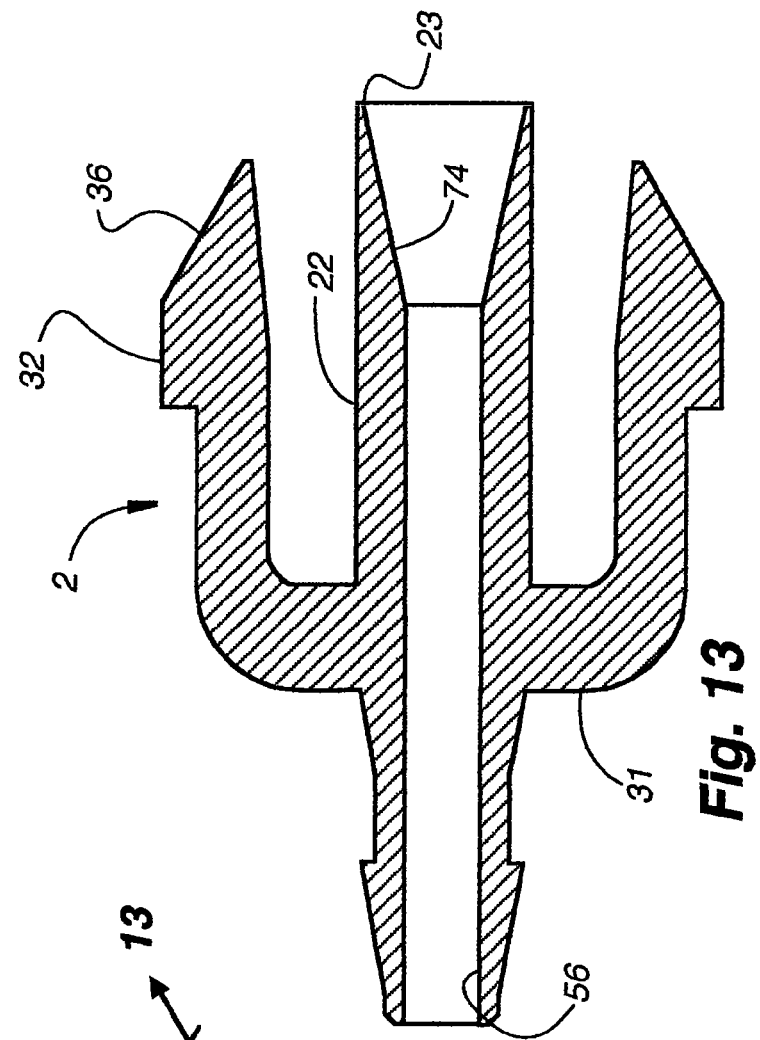
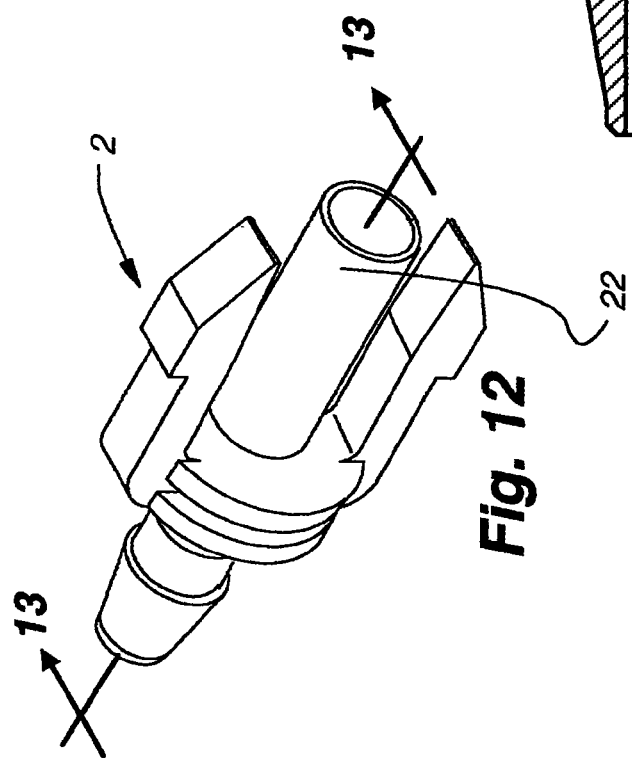

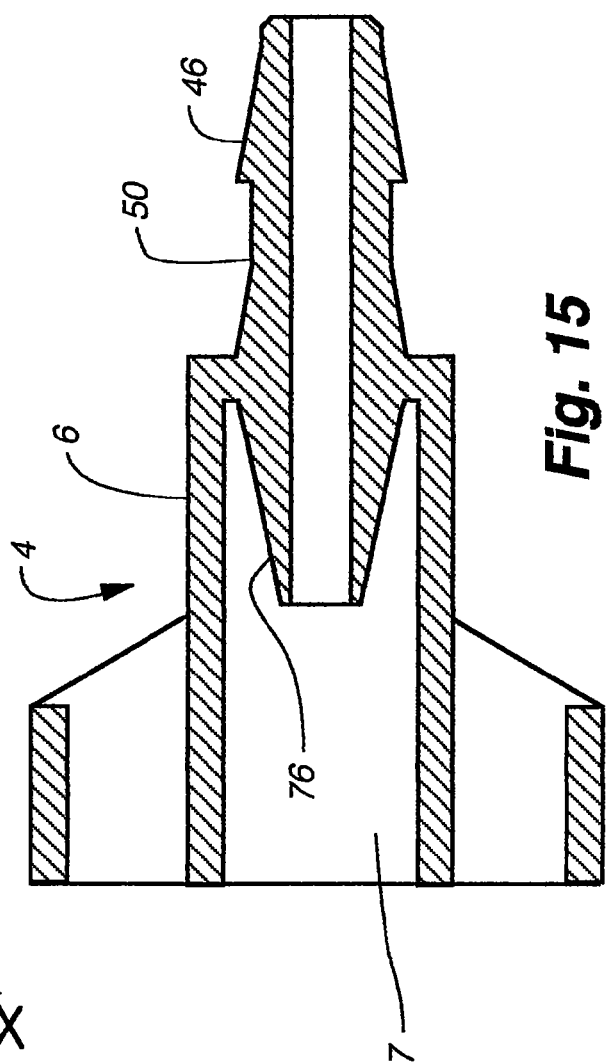
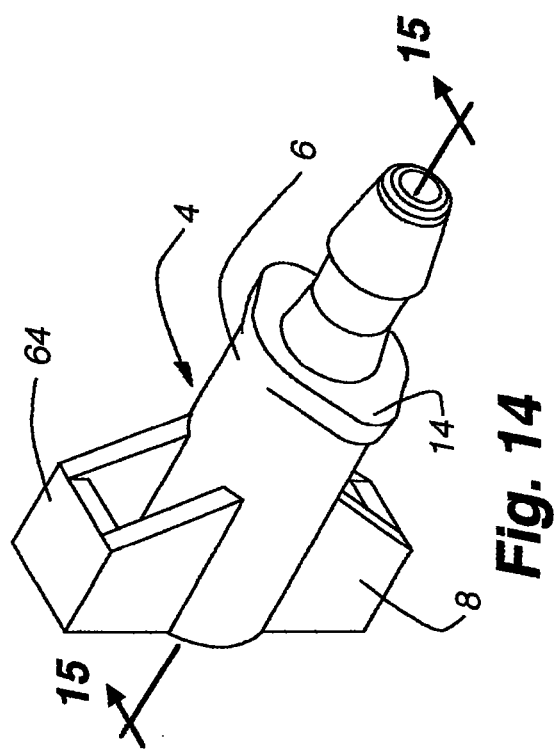

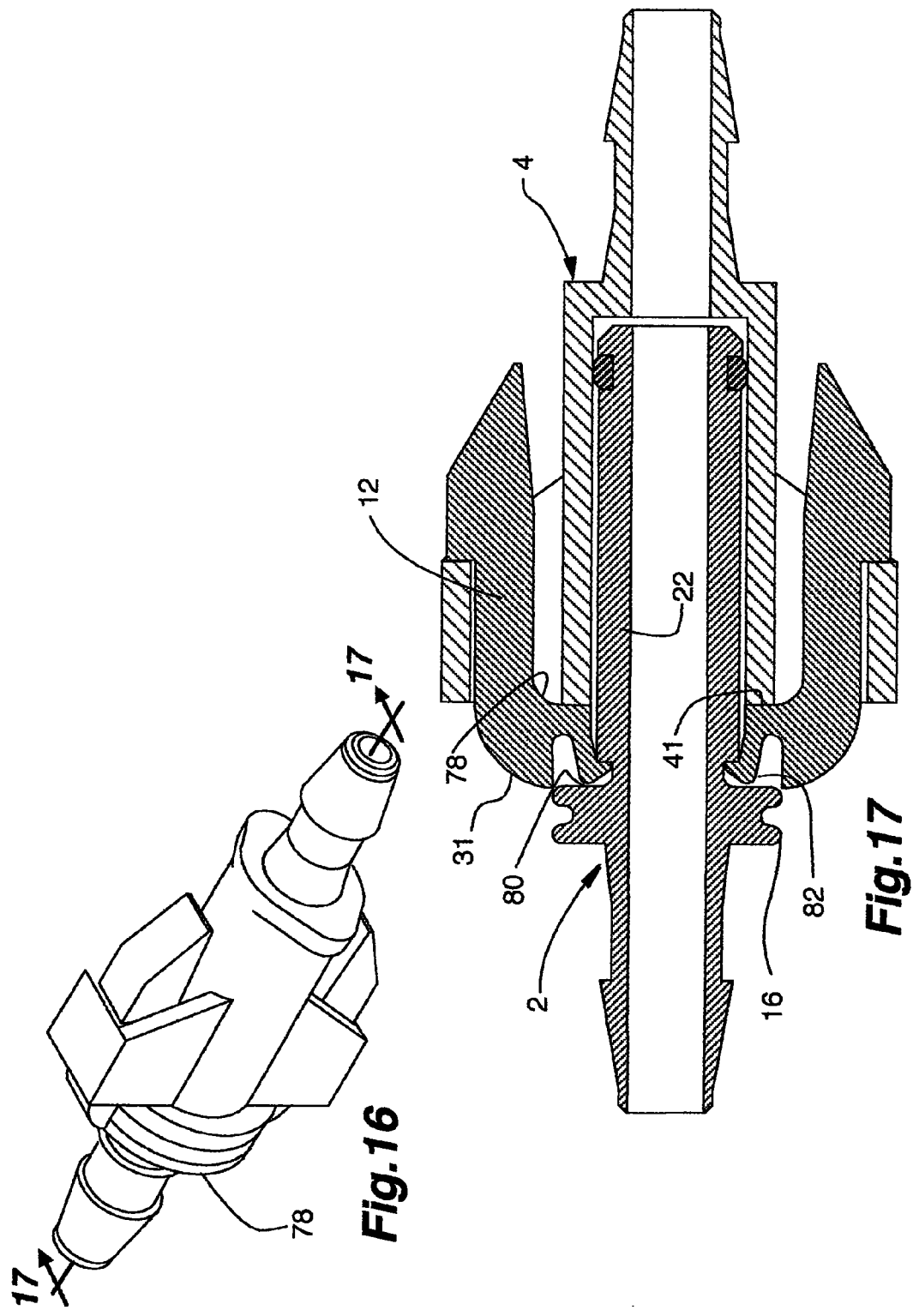

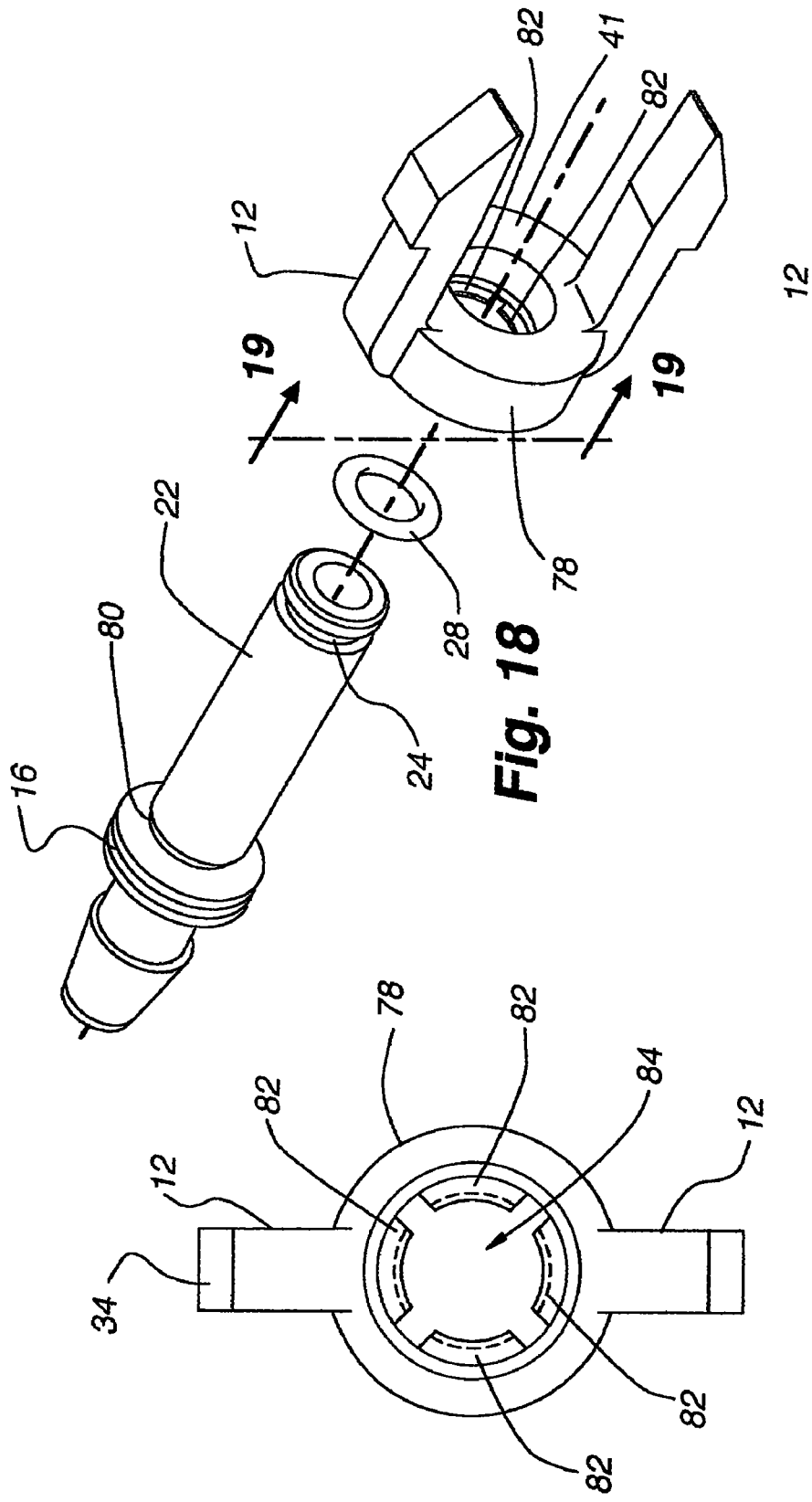

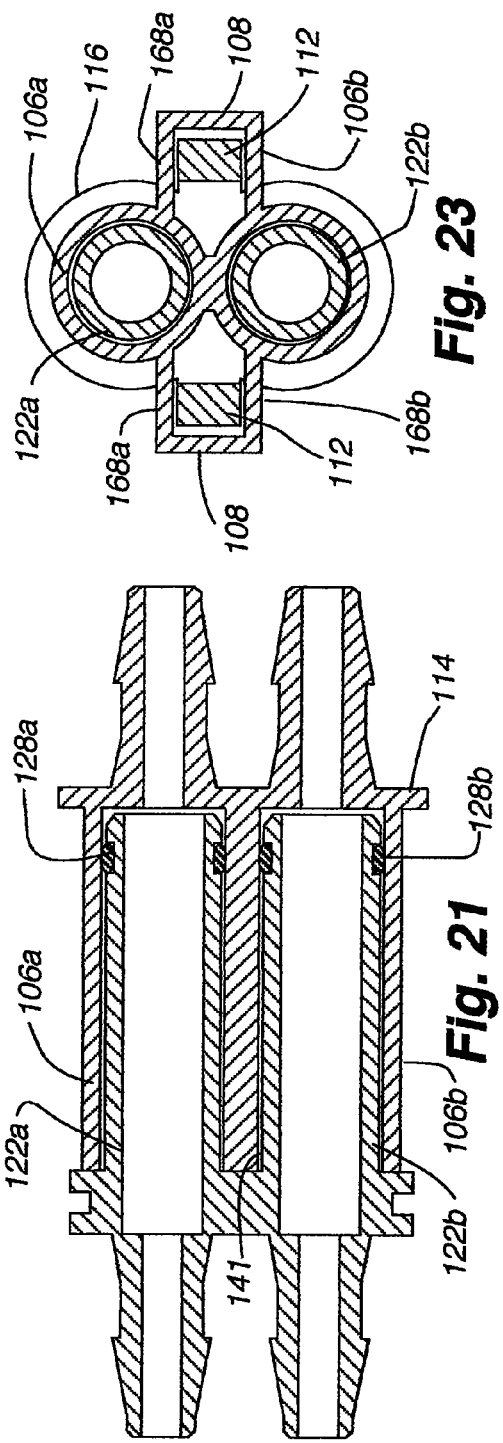

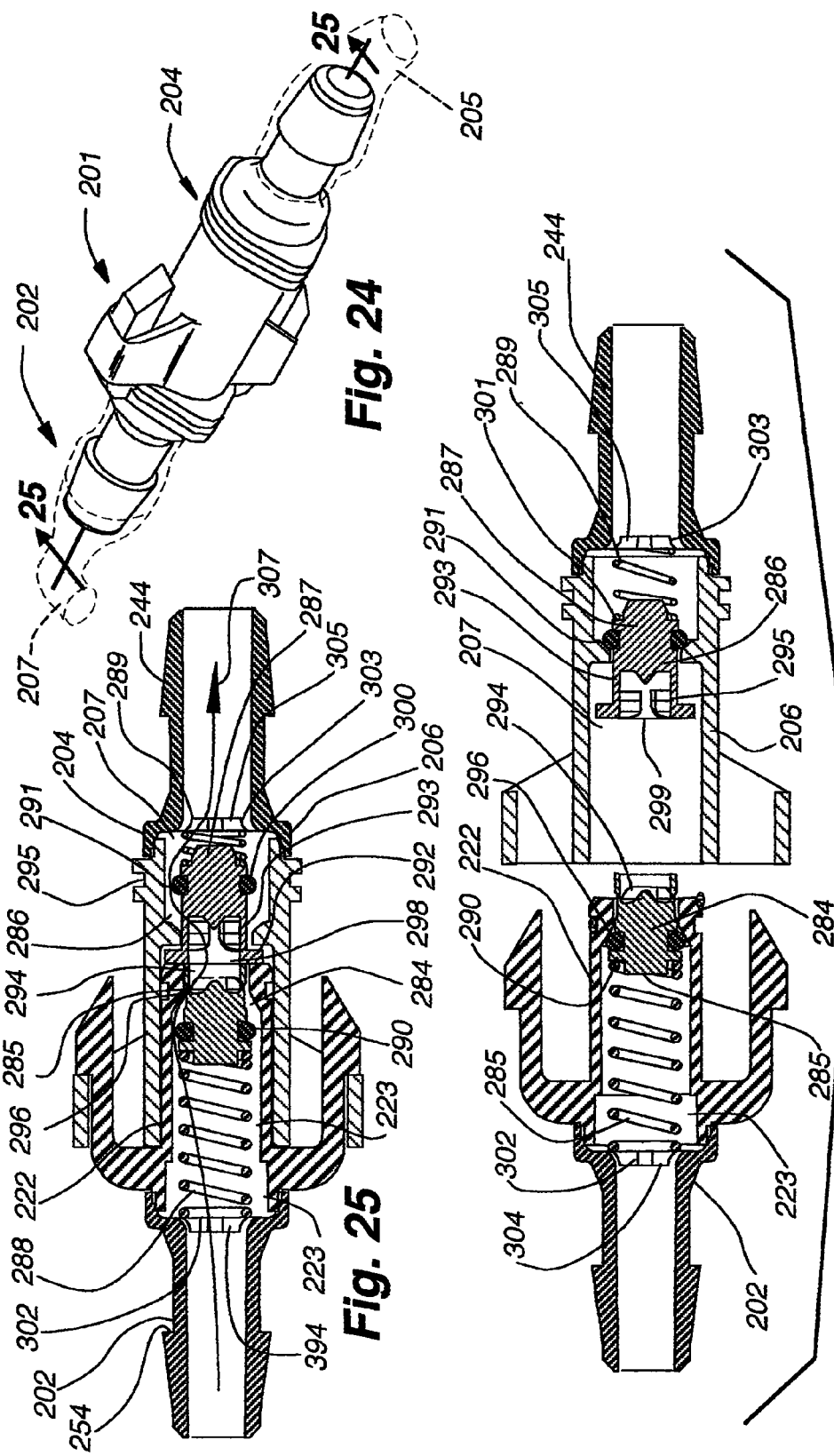

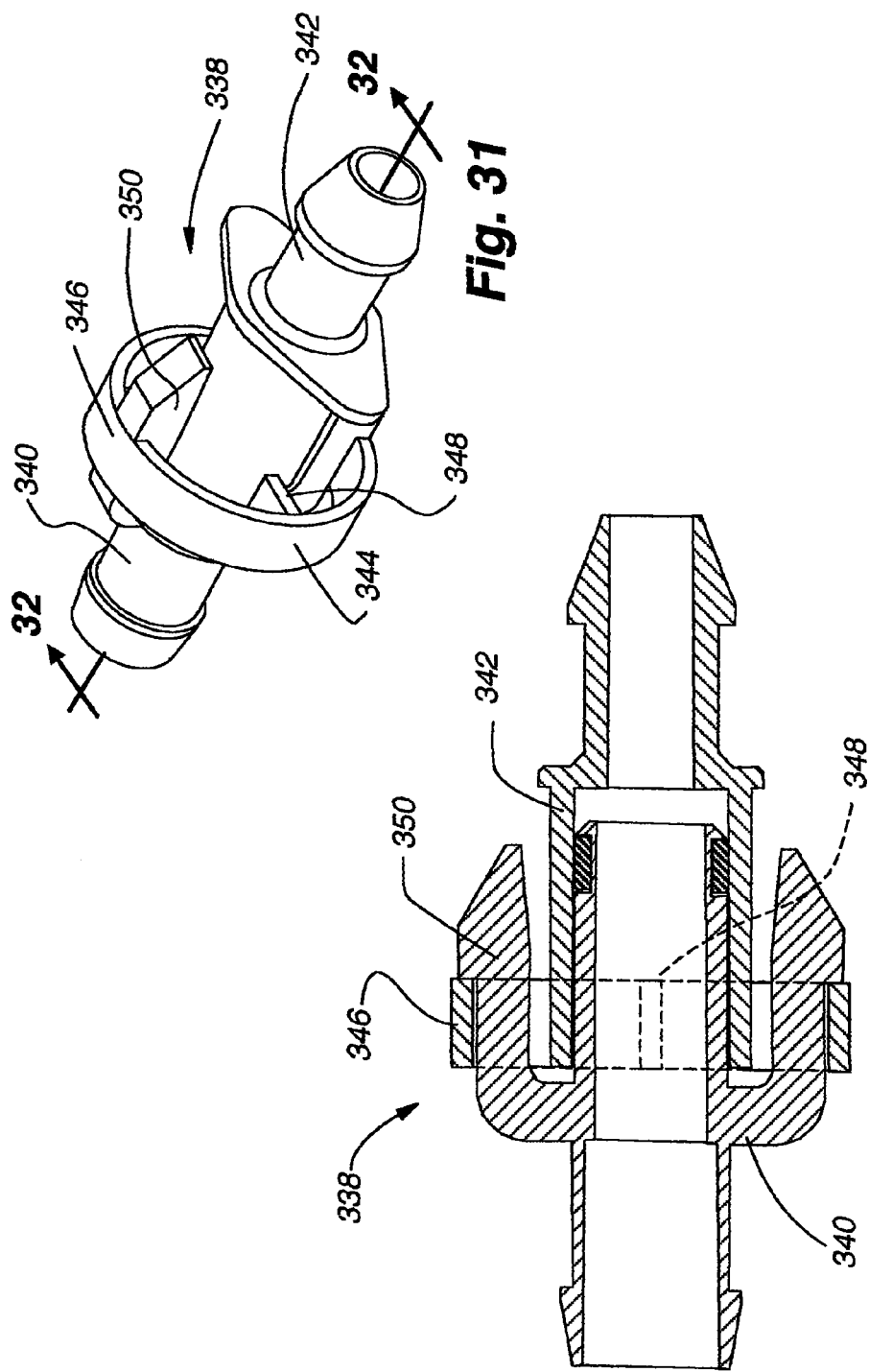

RELEASABLE CONNECTION ASSEMBLY FOR JOINING TUBING SECTIONS

CROSS REFERENCE TO RELATED APPLICATIONS

This application is a continuation patent application of U.S. patent application Ser. No. 10/940,313, filed Sep. 13, 2004 now abandoned and entitled "Releasable Connection Assembly for Joining Tubing Sections," which claims priority to U.S. Provisional Patent Application No. 60/502,325 titled "Releasable Connection Assembly for Joining Tubing Sections," filed Sep. 12, 2003. Both Ser. No. 10/940,313 and 60/502,325 are hereby incorporated by reference herein in their entireties.

BACKGROUND OF INVENTION a. Field of the Invention

This invention relates generally to the field of medical devices used for the transport of both gaseous and liquid fluids and more specifically to a connection assembly for creating a releasable fluid seal connection between two or more sections of tubing.

b. Background Art

Tubing sections, for example, medical tubing, must often be joined together to provide for fluid flow from one medical device to another. It is often desirable, therefore, to connect and disconnect tubing sections from one another. For example, when a patient is provided intravenous fluids, it is often required that an empty fluid bag be replaced with a full fluid bag. It is preferred to merely detach a tubing section connected with the fluid bag to a second tubing section connected with the needle or stent placed intravenously in the patient. In order to switch between the first fluid bag and the second fluid bag, the tubing section connected with the first fluid bag can be disconnected from the second tubing section. The second tubing section can then be easily connected with a tubing section connected with the new fluid bag. This is much simpler than removing the intravenous stent from the patient and replacing it with a new stent directly connected with a new the fluid bag.

Against this backdrop the present disclosure is provided.

SUMMARY OF THE INVENTION

The present invention is fundamentally a releasable connection system for connecting two sections of tubing together. In one embodiment, the releasable connection assembly for connecting a first section of tubing with a second section of tubing includes a male fitting further comprising a male shaft defining a lumen therethrough, at least one clasp operably associated therewith; and a female fitting including a female shaft defining a lumen therethrough, wherein an inner diameter of the female shaft is slightly larger than the outer diameter of the male shaft; and at least one catch is disposed on an outer surface thereof for interfacing with and releasably retaining the clasp.

Further, in an alternative embodiment, the clasp may be rotatably connected to the male shaft, or the catch may be rotatably connected to the female shaft. In this manner the female fitting and male fitting can be rotatably engaged.

In another embodiment of the invention, a releasable connection assembly for connecting a first section of tubing with a second section of tubing includes a male fitting further comprising a male shaft defining a lumen therethrough; a pair of clasps disposed on an outer surface thereof; a sealing member; and a female fitting further comprising a female shaft defining a lumen therethrough, wherein an inner diameter of the female shaft is slightly larger than the outer diameter of the male shaft; and a pair of catches disposed on an outer surface thereof for interfacing with and releasably retaining the pair of clasps on the male fitting respectively; wherein the sealing member engages an inner surface of the female shaft to create a fluid-tight seal between the male fitting and the female fitting.

In a further embodiment, a releasable connection assembly for connecting a plurality of first sections of tubing with a plurality of second sections of tubing includes a first plate containing at least two male fittings, each male fitting further comprising a male shaft defining a lumen therethrough; at least one clasp operably associated with said first plate; and a second plate containing at least two female fittings, each female fitting including a female shaft defining a lumen therethrough, wherein an inner diameter of the female shaft is slightly larger than the outer diameter of the male shaft; and at least one catch is operably associated with the second plate for interfacing with and releasably retaining the clasp on the first plate.

Other features, utilities, and advantages of various embodiments of the invention will be apparent from the following more particular description of embodiments of the invention as illustrated in the accompanying drawings and defined in the appended claims.

BRIEF DESCRIPTION OF THE DRAWINGS

FIG. 6 is an isometric view of the male fitting of the type depicted in FIG. 1.

FIG. 7 is a cross-section view of the male fitting as indicated in FIG. 6.

FIG. 8 is an isometric view of the female fitting of the type depicted in FIG. 1.

FIG. 9 is a cross-section view of the female fitting as indicated in FIG. 8.

FIG. 10 is an isometric view of a releasable connection assembly joining two sections of tubing according to another embodiment of the invention.

FIG. 11 is a cross-section view of the connection assembly as indicated in FIG. 10.

FIG. 12 is an isometric view of the male fitting of the connection assembly of FIG. 10.

FIG. 13 is a cross-section view of the male fitting as indicated in FIG. 12.

FIG. 14 is an isometric view of the female fitting of the connection assembly of FIG. 10.

FIG. 15 is a cross-section view of the female fitting as indicated in FIG. 14.

FIG. 16 is an isometric view of a releasable connection assembly according to another embodiment of the invention.

FIG. 17 is a cross-section view of the connection assembly as indicated in FIG. 16.

FIG. 18 is an exploded isometric view of the male fitting of the connection assembly of FIG. 16.

FIG. 19 is in an end plan view of the distal end of the male fitting of the connection assembly of FIG. 18.

FIG. 21 is a cross-section view of the connection assembly as indicated in FIG. 20.

FIG. 22 is a cross-section view of the connection assembly as indicated in FIG. 20.

FIG. 23 is a cross-section view of the connection assembly as indicated in FIG. 20.

FIG. 24 is an isometric view of a releasable connection assembly including stop-flow valves according to another embodiment of the invention.

FIG. 25 is a cross-sectional view of a releasable connection assembly as indicated in FIG. 24

FIG. 26 is a cross-sectional view of the shut-off valve when the connection assembly is disconnected.

FIG. 31 is a perspective view of a connector assembly having a fixed receiving collar to allow at least some rotation of the male connector portion within the female connector portion.

FIG. 32 is a cross-sectional view of the fixed receiving collar embodiment as indicated in FIG. 31.

DETAILED DESCRIPTION OF INVENTION

A first exemplary releasable connection assembly 1 according to the present invention is depicted, either in whole or in part, in FIGS. 1-9. The connection assembly includes two structures, a male fitting 2 and a female fitting 4. The male fitting 2 is shown in greater detail in FIGS. 2, 4, 6, and 7. The female fitting 4 is shown in greater detail in FIGS. 2, 4, 8, and 9.

Figure 1:
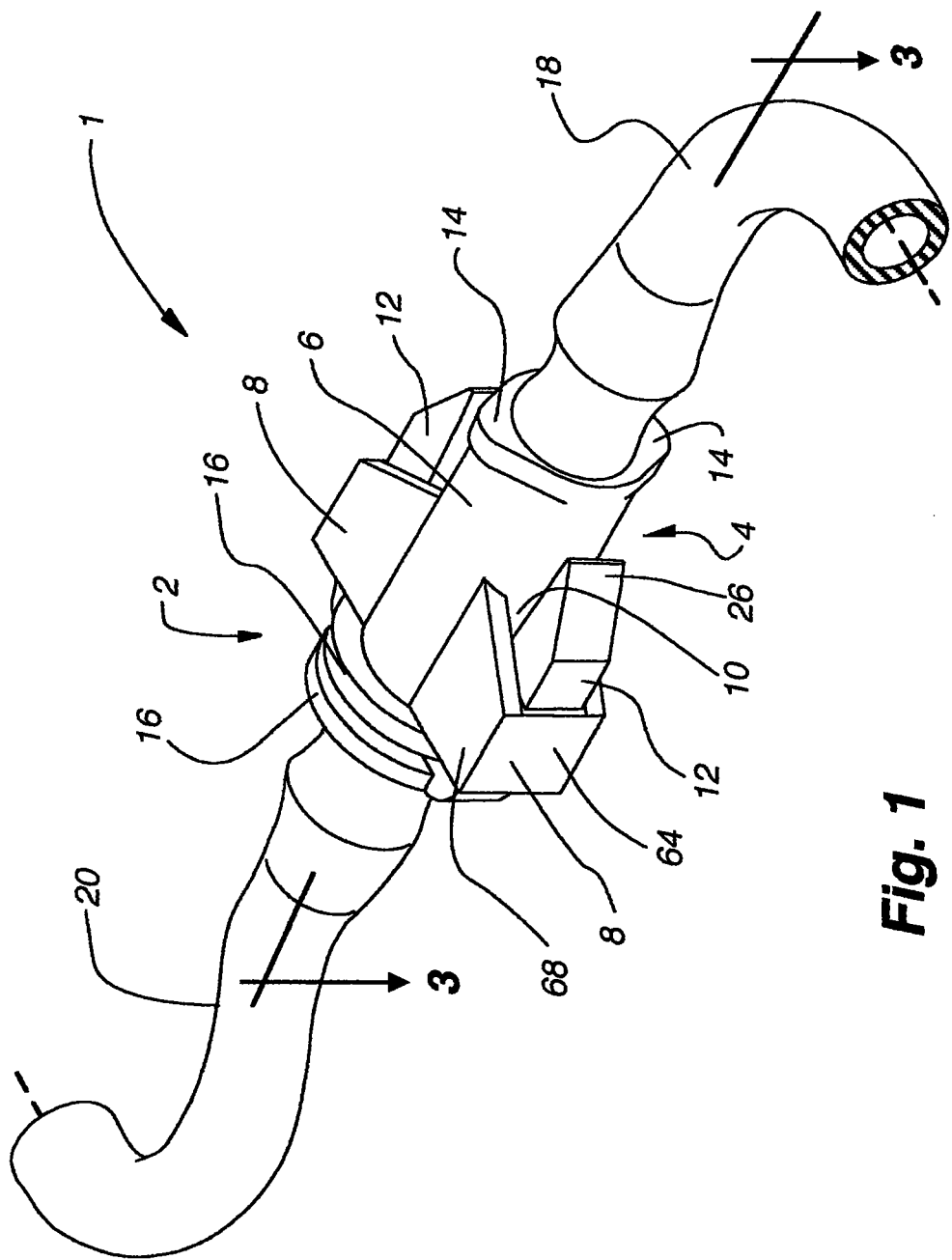
FIG. 1 is an isometric view of a releasable connection assembly joining two sections of tubing according to an embodiment of the invention.
Figure 2:
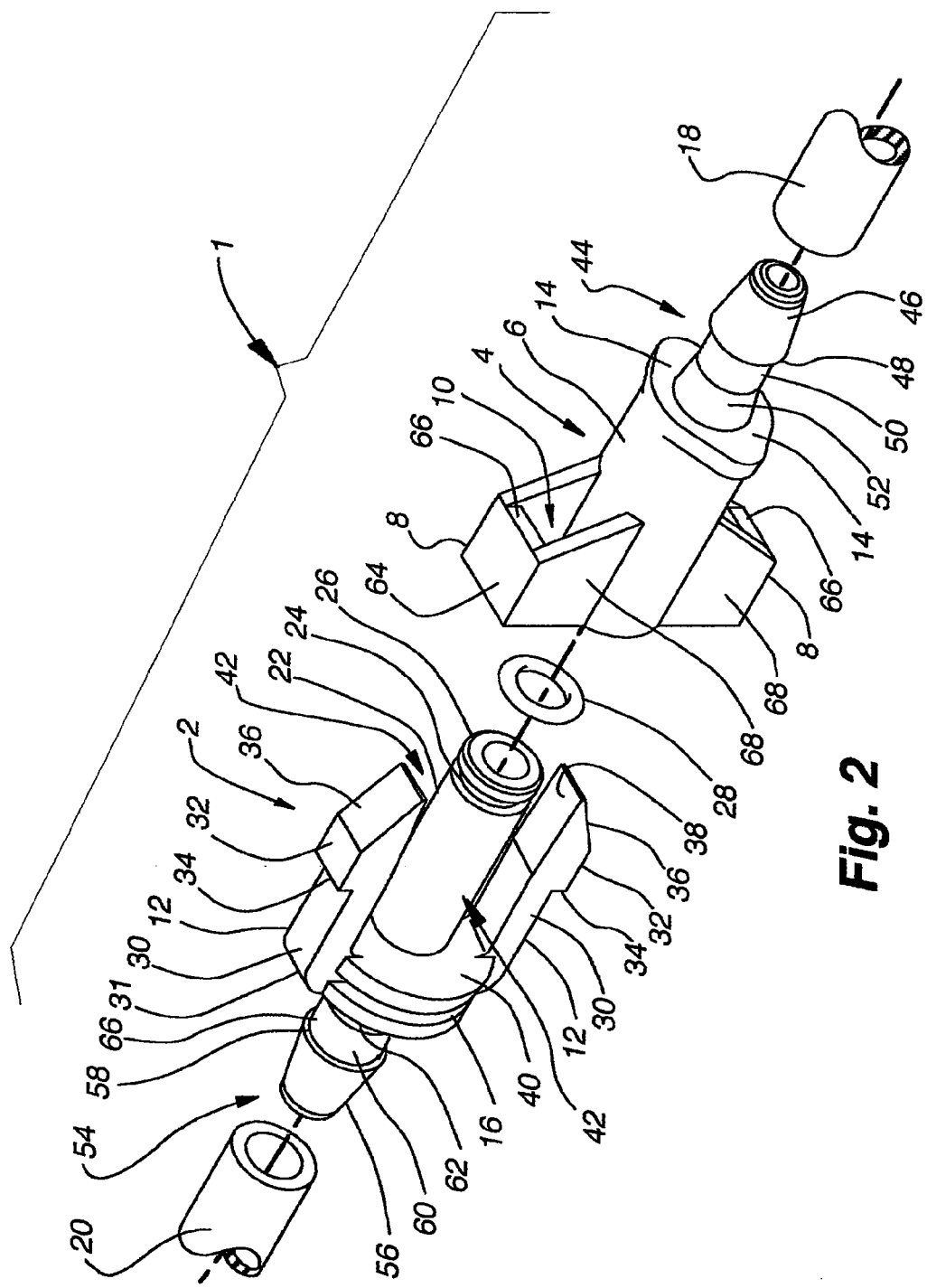
FIG. 2 is a an exploded isometric view of the connection assembly and tubing of FIG. 1.
Figure 3:
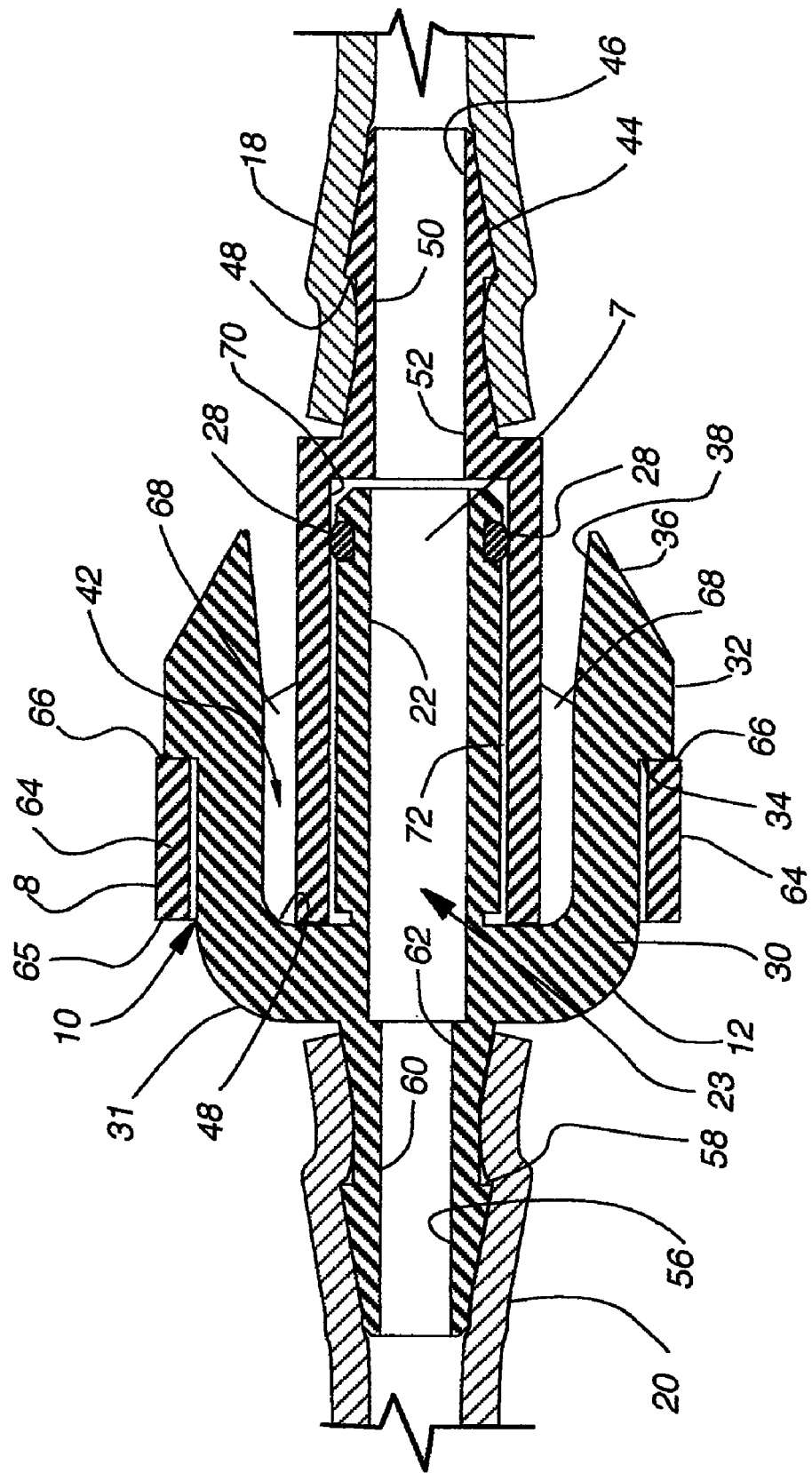
FIG. 3 is a cross-section of the connection assembly and tubing as indicated in FIG. 1.

The male fitting 2 connects with the female fitting 4 as best shown in cross-section in FIG. 3. A first tubing section 18 connects with a first tubing coupling 44 (see also FIG. 2) on the distal end of the female fitting 4, and a second tubing section 20 connects with a second tubing coupling 54 on the proximal end of the male fitting 2. The orientations "proximal" and "distal" as used herein have been arbitrarily chosen, but will follow the convention just described with reference to the ends of the female fitting 4 and male fitting 2 with the first and second tubing coupling 44, 54, respectively.

The primary component of the female fitting 4 is a female shaft 6 defining a first cylindrical lumen 7. The first tubing coupling 44 extends from the distal end of the female shaft 6. The first tubing coupling 44 includes a cannula portion 46 shaped as a frustum tapering toward the distal end. The proximal end of the cannula portion 46, i.e., at the larger diameter of the frustum, connects with a coupling shaft 50 of a narrower outer diameter than that of the proximal end of the cannula portion 46. The difference in outer diameters results in an annular shelf that functions as a coupling barb 48. As the coupling shaft 50 extends proximally toward the female shaft 6, the outer diameter gradually widens into a coupling flange 52 that ultimately interfaces with the distal end of the female shaft 6.

An oblong grip flange 14 may be provided at the distal end of the female shaft 6. The narrower diameter of the oblong grip flange 14 may be equal to the outer diameter of the female shaft 6. The wider diameter of the oblong grip flange 14 is then wider than the diameter of the female shaft 6 to provide flange extensions on opposite sides of the female shaft 6 to provide easy gripping surfaces. Note that flange shapes are not critical as long as the flange provides an enhance gripping surface for the user.

A pair of catches 8 may be formed on opposite sides of the outer surface of the female shaft 6 at the proximal end. The catches 8 may further be oriented in positions 90° (or any other functional angles) about the female shaft 6 apart from the positions of the wide diameter portions of the oblong grip flange 14. Each of the catches 8 may include two trapezoidal side walls 68, spaced apart from and parallel to each other, and extending generally normally from the outer surface of the female shaft 6. An end wall 64 connects the ends of the side walls 68 opposite the surface of the female shaft 6 to form a slot 10. A retention surface 66 may be provided by the distal face of the end wall 64 for aiding the retention of the male fitting 2 as described later herein.

The primary component of the male fitting 2 is a male shaft 22, which in this first embodiment may be a cylindrical wall defining a second cylindrical male shaft lumen 23. A first annular recess 24 may be formed in the outer surface of the male shaft 22 adjacent to, but spaced apart from the distal end 26 of the male shaft 22. An O-ring 28 may be seated within the first annular recess 24 for creating a fluid-tight seal with the female fitting 4 as will be further described herein.

The second tubing coupling 54 extends from the proximal end of the male shaft 22. The second tubing coupling 54 includes a cannula portion 56 shaped as a frustum tapering toward the proximal end. The distal end of the cannula portion 56, i.e., at the larger diameter of the frustum, connects with a coupling shaft 60 of a narrower outer diameter than that of the distal end of the cannula portion 56. The difference in outer diameters results in an annular shelf that functions as a coupling barb 58. As the coupling shaft 60 extends distally toward the male shaft 22, the outer diameter gradually widens into a coupling flange 62 that ultimately interfaces with the proximal end of the male shaft 22.

One or more annular grip ribs 16 may also be formed about the outer surface of the proximal end of the male shaft 22. The diameter of each of the annular grip ribs 16 is larger than the outer diameter of the male shaft 22, thereby providing a good grasping surface for a user. A pair of clasps 12 may each be formed primarily of a tang 30 extending spaced apart from the male shaft 22 and parallel to the axis of male shaft 22. The proximal ends of the tangs 30 may form an elbow 31 and connect with the proximal end of the male shaft 22 at the location of the annular grip ribs 16. The annular grip ribs 16 may provide reinforcement to the connect of the tangs 30 with the male shaft 22. The tangs 30 may extend almost the entire length of the male shaft 22. The distal ends of the tangs 30 may each be formed with a clasp tab 32 protruding in a direction normal to the outer surface of the male shaft 22 adjacent the respective clasp 12. The tang 20 distal to the clasp tab 32 may have an outer taper 36 and an inner taper 38.

Figure 4:
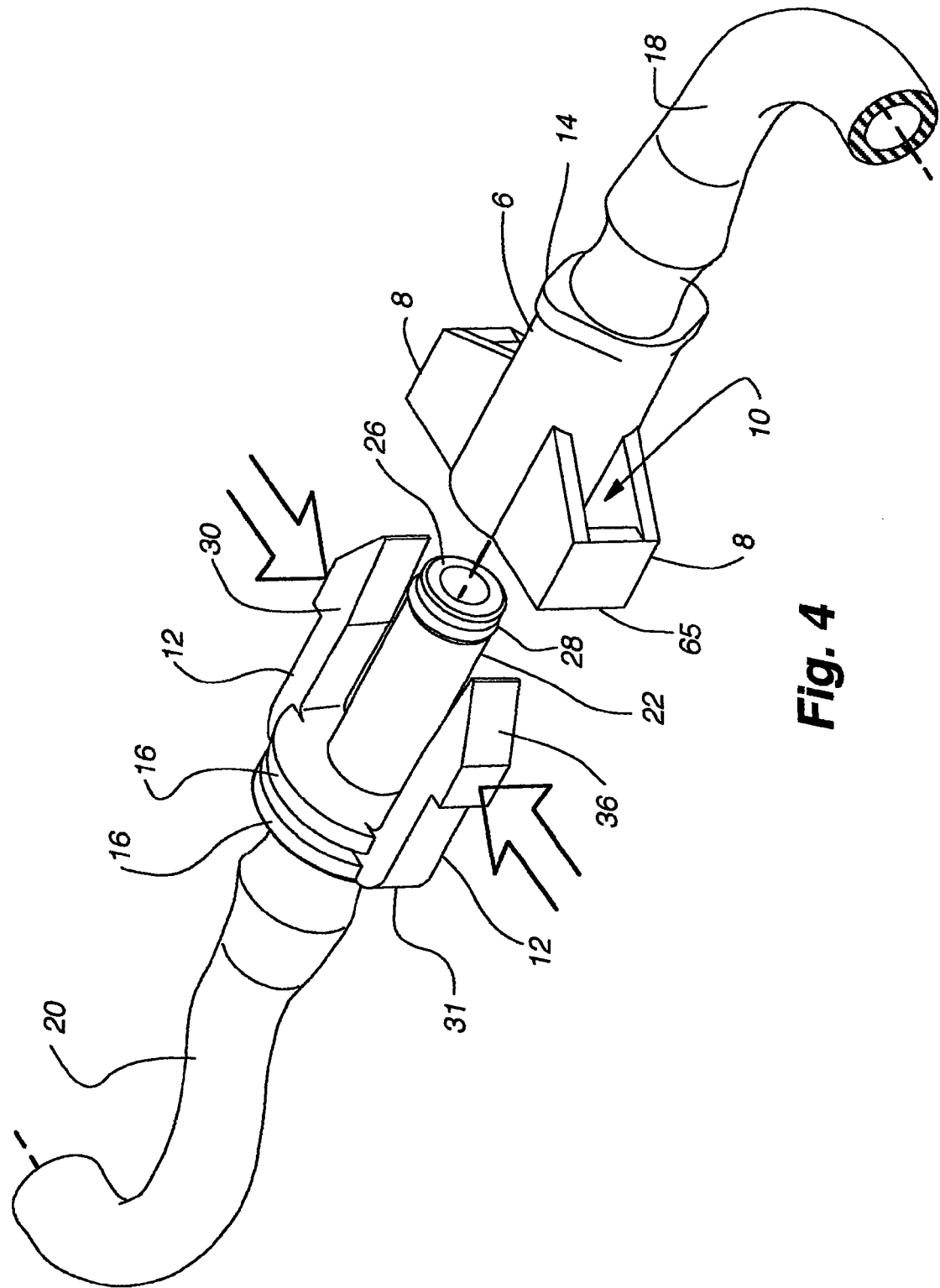
FIG. 4 is an isometric view of the connection assembly of FIG. 1 with the male fitting and female fitting separated and indicating the direction of force to be applied to the biased tabs for connection.
Figure 5:
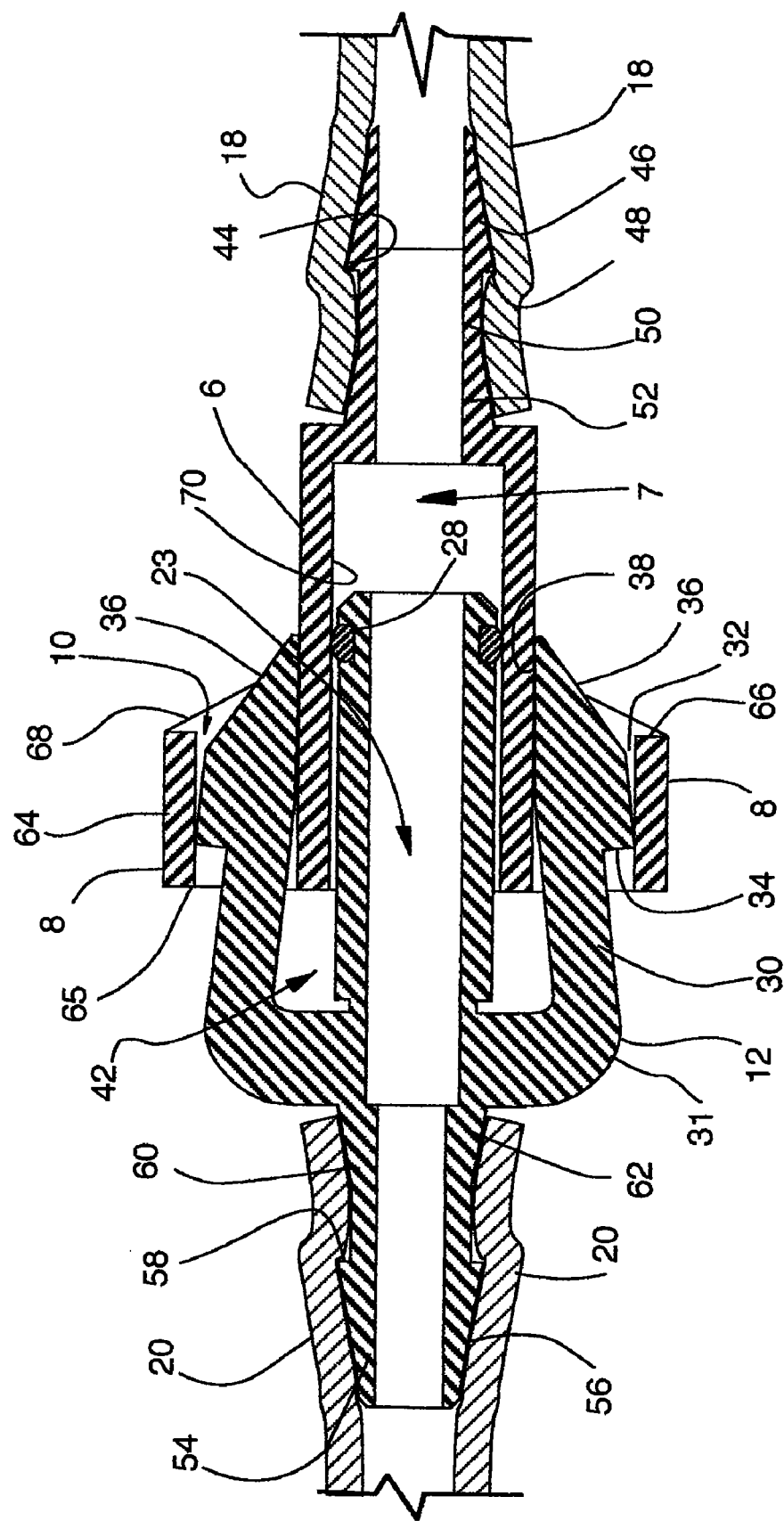
FIG. 5 is a representative cross-section of the connection assembly of the type depicted in FIG. 1 with the male fitting partially engaged with the female fitting.
Figure 20:
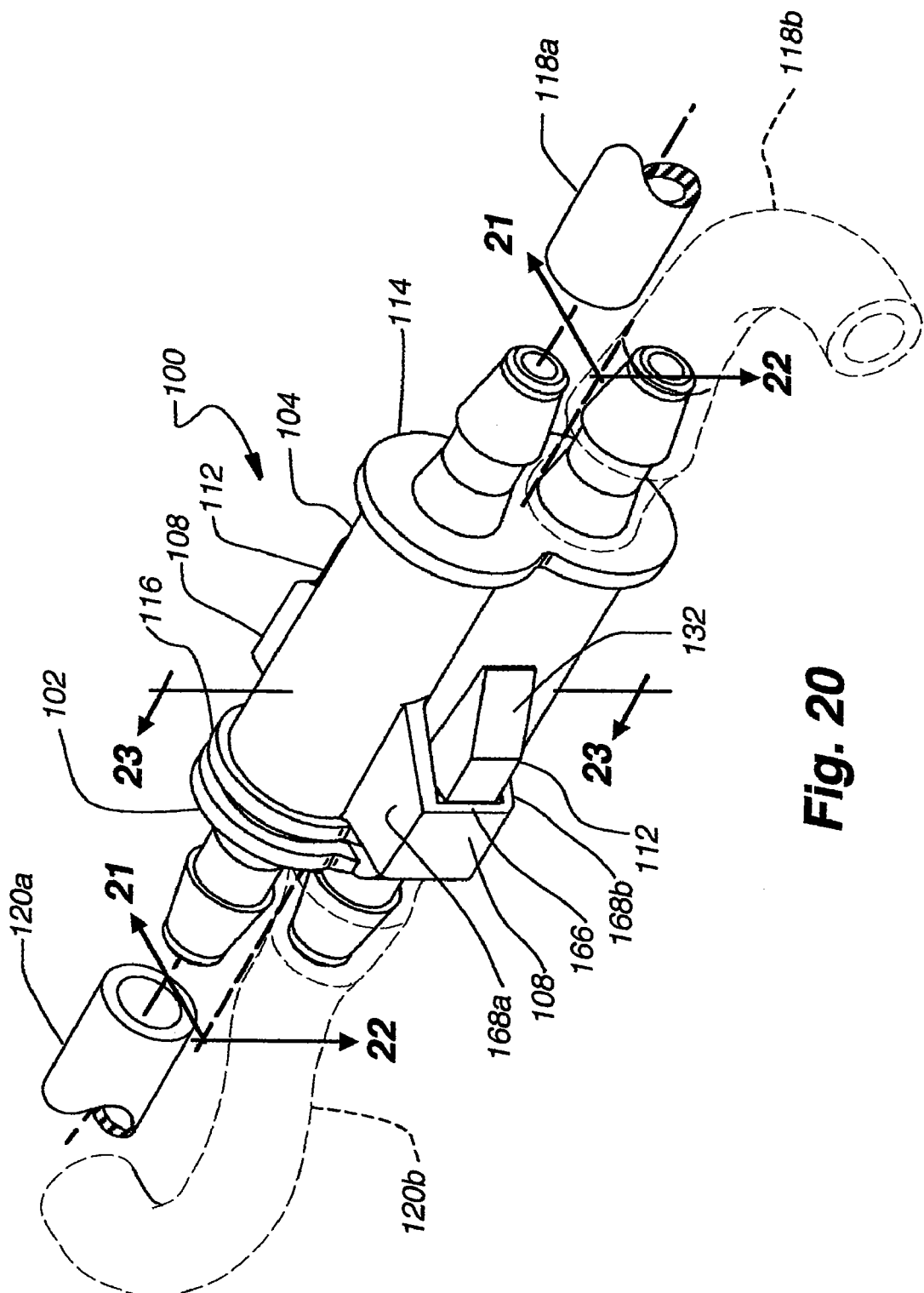
FIG. 20 is an isometric view of a releasable connection assembly joining two pairs of two sections of tubing according to another embodiment of the invention.

As shown in FIGS. 3-5, the male fitting 2 and the female fitting 4 connect with each other to form the connection assembly 1 by the insertion of the male shaft 22 into the lumen 7 of the female shaft 6. The connection assembly 1 is further held together by the insertion of the tangs 30 of the clasps 12 into the slots 10 of the catches 8 and the interface between the clasps 12 and the catches 8. Each of the tangs 30 of the clasps 12 is attached to the male shaft 22 at the proximal end via an elbow section 31 extending normally from the outer surface 72 of the male shaft 22, but is otherwise separated from the outer surface 72 of the male shaft 22 by a slip gap 42. The slip gap 42 provides a space to allow the female shaft 6 to slide between the tangs 30 of the clasps 12 and the male shaft 22 until it abuts the mating surface 40 of the male shaft 22. The diameter of the inner surface 70 of the female shaft 6 defining the first lumen 7 is slightly larger than the diameter of the outer surface 72 of the male shaft 22, allowing for a close fit. The O-ring 28 on the proximal end 26 of the male shaft 22 is of a larger diameter than the outer surface 72 of the male shaft 22 and interfaces with the inner surface 70 of the female shaft 6 to create a fluid-tight seal between the male fitting 2 and the female fitting 4.

The tangs 30 of the clasps 12 are biased in a direction normal to the outer surface 72 of the male shaft 22 (note, however, that the tangs and clasps of the invention may also be non-normal to the outer surface as long as the interaction is functional). As shown in FIG. 4, the tangs 30 must be forced radially inward toward the male shaft 22 in order for the tangs 30 to fit through the slots 10 in the catches 8. This inward force may be supplied by the user squeezing the clasps 12 toward each other when inserting the male shaft 22 into the female shaft 6. Alternately, the inward force may be provided by the interaction between the clasps 12 and the catches 8 when a user pushes the male fitting 2 and the female fitting 4 axially together. In this case, the outer tapers 36 of the tangs 30 engage the leading surfaces 65 of the catches 8. As the axial force is applied to the male fitting 2 and female fitting 4, the outer tapers 36 slide against the leading surfaces 65 and force the tangs 30 to bend radially inward at flex points provided by the elbows 31.

As shown in FIG. 5, the inner tapers 38 decrease the required height of the catch slot 10 to allow passage of the tangs 30 therethrough, and therefore, also decrease the amount of flex required of the clasps 12 at the elbows 31, thereby reducing strain and providing greater resiliency of the clasps 12. The clasp tabs 32 are pronounced, raised sections of the clasps 12 toward the proximal ends of the tangs 30 that create a retention shelf 34 on each of the clasps 12. Once the length of the clasp tabs 32 pass through the catch slots 10, the inward radial force on the clasps 12 releases and the bias of the clasps 12 forces the clasps 12 radially outward to their original position substantially parallel to the male shaft 22. Upon return of the clasps 12 to their original position, the retention shelves 34 engage the retention surface 66 of the catches 8, thereby preventing the male fitting 2 from being pulled apart from the female fitting 4. In order to release the male fitting 2 from the female fitting 4, the user must push the clasps 12 radially inward to disengage the retention shelves 34 from the retention surfaces 66 of the catches 8. The user can then apply an axial pulling force to the male fitting 2 and female fitting 4 to separate the two portions of the connection assembly 1.

As shown in FIGS. 1 and 3-5, the female fitting 4 is connected with the first tubing section 18 via the first tubing coupling 44. The user may push one end of the first tubing section 18, which is generally a pliable, elastomeric material, over the cannula 46 of the first tubing coupling 44. The gradually increasing taper of the cannula 46 expands the diameter of the first tubing section 18. The first tubing section 18 then passes over a narrower coupling shaft 50 of the first tubing coupling 44, which allows the diameter of the first tubing section 18 to constrict toward its original diameter size. The first tubing coupling 44 then expands in diameter again to form a coupling shaft flange 52 against which the inner surface of the first tubing 18 section snugly fits. The interface between the cannula 46 and the coupling shaft 50 forms a coupling barb 48 that acts to resist the disengagement of the first tubing section 18 from the first tubing coupling 44. The coupling shaft flange 52 aids in this resistance by pinching the first tubing section 18 against the coupling shaft 50 and the coupling barb 48.

Similarly, the male fitting 2 is connected with the second tubing section 20 via the second tubing coupling 54. The user may push one end of the second tubing section 20, which is generally a pliable, elastomeric material, over the cannula 56 of the second tubing coupling 54. The gradually increasing taper of the cannula 56 expands the diameter of the second tubing section 20. The second tubing section 20 then passes over a narrower coupling shaft 60 section of the second tubing coupling 54, which allows the diameter of the second tubing section 20 to constrict toward its original diameter size. The second tubing coupling 54 then expands in diameter again to form a coupling shaft flange 62 against which the inner surface of the second tubing section 20 snugly fits. The interface between the cannula 56 and the coupling shaft 60 forms a coupling barb 58 that acts to resist the disengagement of the second tubing section 20 from the second tubing coupling 54. The coupling shaft flange 62 aids in this resistance by pinching the second tubing section 20 against the coupling shaft 60 and the coupling barb 58. Note that other attachment means between the tubing and male fitting are also envisioned to be within the scope of the present invention.

Preferably, the inner diameters of the first tubing section 18, the second tubing section 20, the first tubing coupling 44, the second tubing coupling 54, and the male shaft 22 are all of generally the same diameter to provide for generally constant fluid flow rate, pressure, and volume throughout the connection assembly 1. However, if a change in pressure, flow rate, or flow volume were desired, the diameters of each of these sections could be designed to achieve a desired result.

FIGS. 6 and 7 provide a detailed view of the male member 2 uncoupled or disconnected from the female member 4. Note the position of the O-ring 28 within a groove 24 defined around the male shaft 22. FIGS. 8 and 9 provide a detailed view of the female member 4 uncoupled or disconnected from the male member 2.

In another embodiment of the invention as shown in FIGS. 10-15, an alternative fluid seal design may be used. Instead of an O-ring 28 on the exterior surface of the male shaft 22 as, for example, depicted in FIGS. 3-4, and 7 the male fitting 2 is formed with a thick walled male shaft 22 with a tapered inner surface 74 defining the male shaft lumen 23 on the distal end of the male shaft 22. Correspondingly, a tapered cannula 76 is formed within the female shaft lumen 7 of the female fitting 4 toward the distal end. The tapered cannula 76 is designed to interface with the tapered inner surface 74 of the male shaft 22 to create a fluid-tight seal or face seal when the male fitting 2 and the female fitting 4 are connected with each other. See FIG. 11.

FIG. 13 provides a cross-sectional view along line 13-13 of FIG. 12 illustrating the tapered inner surface 74 of the male shaft 22. FIG. 15 provides a cross-sectional view along line 15-15 of FIG. 14 illustrating the tapered cannula 76 formed within the female shaft lumen 7. The frictional engagement between tapered inner surface 74 and the tapered cannula 76 provides a fluid-tight seal (see FIG. 11).

In another embodiment of the invention as shown in FIGS. 16-19, the clasps 12 are not integrally formed with the male fitting 2, but are instead integral with a collar 78 that may itself be rotationally attached to the male shaft 22. The collar 78 joins the elbows 31 of the clasps 12. The diameter of the collar 78 is smaller than the separation of the tangs 30 of the clasps 12. The interior surface of the collar 78 defines a collar lumen 84 into which four detents 82 may radially extend (see FIG. 19). The collar lumen 84 is slightly larger in diameter than the outer diameter of the male shaft 22, while the projection of the detents 82 extend a distance such that the diameter between opposing detents 82 is slightly smaller than the outer diameter of the male shaft 22. A second annular recess 80 may be formed in the exterior surface of the male shaft 22 adjacent to and distal to the annular grip ribs 16. The detents 82 are snapped into the second annular recess 80 when the collar 78 is pushed axially along the male shaft 22 and into place.

The proximal end of the female shaft 6 may interface with a collar mating surface 41 rather than the proximal mating surface 40 of the first embodiment as shown in at least FIGS. 2 and 3. The detents 82 are flexible enough to bend when forced against the outer surface of the male shaft 2, but are biased to return to their original radial positions when engaged in the second annular recess 80, thereby retaining the collar 78 and clasps 12 on the male shaft 22. Because the clasps 12 are not integrally formed with the male shaft 22 in this embodiment, the collar 78 and the connected clasps 12 are free to rotate about the male shaft 22. This configuration allows the male fitting 2 and the female fitting 4 to rotate axially with respect to each other to provide increased flexibility of the connection assembly 1.

Another embodiment of a connection assembly 100 is shown in FIGS. 20-23 for connecting two sets of two tubing sections 118a, 118b, 120a, and 120b. In this embodiment, a male fitting 102 includes a first male shaft 122a and a second male shaft 122b connected with each other at the proximal end by a pair of grip ribs 116, but otherwise spaced apart from each other by interior gap 141 (see FIG. 21). The grip ribs 116 are annular flanges about the outer surfaces of each of the first male shaft 122a and the second male shaft 122b that are integrally connected with each other to form a figure-8 span holding the first male shaft 122a and the second male shaft 122b together. A female fitting 104 includes a first female shaft 106a and a second female shaft 106b that are joined together along the length of their exterior surfaces. A grip flange 114 is also formed as a contiguous figure-8 about the exterior surface of the distal ends of the first female shaft 106a and the second female shaft 106b. The catches 108 are attached to the exterior surfaces of both the first female shaft 106a and the second female shaft 106b. A first side wall 168a of each of the catches 108 is attached to the first female shaft 106a and a second side wall 168b of each of the catches 108 is attached to the second female shaft 106b (see FIG. 23).

Still referring to FIGS. 20-23, the first male shaft 122a and the second male shaft 122b slide within the first female shaft 106a and the second female shaft 106b, respectively, just as in the first embodiment described herein with respect to FIGS. 1-9. As depicted in FIG. 21, the first male shaft 122a and the second male shaft 122b may create a fluid-tight seal with the first female shaft 106a and the second female shaft 106b, respectively, by seating a first O-ring 128a between the inner surface of the first female shaft 106a and the outer surface of the first male shaft 122a and similarly by seating a second O-ring 128b between the inner surface of the second female shaft 106b and the outer surface of the second male shaft 122b. Alternatively, a fluid-tight seal could be provided using cannulas and tapered lumen interfaces as described herein with respect to FIGS. 10-15. As in the first embodiment of FIGS. 1-9, the clasps 112 engage with and are retained by the catches 108 to actively hold the male fitting 102 and female fitting 104 together. The male fitting 102 may be released from retention by the female fitting 104 by forcing the clasps 112 radially inward to disengage the clasp tabs 132 from the retention surfaces 166 and pulling the male fitting 102 and the female fitting 104 apart.

It should be apparent that additional male and female fittings could be integrated together to form connection assemblies for connecting three, four, or more sets of tubing sections. The male and female fittings could be integrated together side by side to lie in a single plane, or stacked upon each other to form triangular, square, pentagonal, or other formations and arrangements. In addition, embodiments of the present invention may include one, three, seven or any number of clasps or catches. Note also that there could be a greater number of clasps of catches within any one embodiment to allow for adjustable rotatable orientation of connections.

Another embodiment of a releasable connection assembly 201 is shown in FIGS. 24-26. In this embodiment, the male fitting 202 and the female fitting 204 are each provided with shut-off valves 284, 286 respectively, to halt fluid flow from the sections of tubing 205 and 207 when the male fitting 202 and the female fitting 204 are disengaged from each other. The male fitting 202 has a first shut-off valve 284 arranged within the lumen 223 of the male shaft 222. Similarly, the female fitting 204 has a second shut-off valve 286 arranged within the lumen 207 of the female shaft 206.

The male fitting shut-off valve 284 is constructed primarily of a first valve body 285 and a first spring 288. The first valve body 285 is positioned toward the distal end of the male shaft 222. The distal end of the first spring 288 is connected with the proximal end of the first valve body 285 while the proximal end of the first spring 288 is connected with a first cap 302 that fixedly interfaces with the proximal end of the male shaft 222 to provide a stationary anchor for the first spring 288. The first cap 302 also tapers proximally to form a first fluid port 304 extending into a lumen defined by the second tubing coupling 254. Rather than being integrally formed with the male fitting 202, in this embodiment the first cap 302 may be directly attached to the male shaft 222 or it may be sandwiched between the second tubing coupling 254 and the male shaft 222. In the latter case, the first cap 302 may be fastened to the proximal end of the male shaft 222 by means of, but not limited to, welding, adhesive, snap-fit or over-molding, to allow for the prior insertion of the first shut-off valve 284 during assembly of the male fitting 202.

The distal end of the lumen 223 in the male shaft 222 tapers slightly to reduce the diameter of the lumen 223 at the distal end of the male shaft 222. The diameter of the first valve body 285 is slightly smaller than the diameter of the lumen 223 distal from the male tapered portion 296. The proximal end of the first valve body 285 is also encompassed by a first valve O-ring 290, which is slightly smaller in diameter than the lumen 223 proximal to the male tapered portion 296. The distal end of the first valve body 285 defines first valve flues 294 separated by first valve collar supports 292, which support a first valve collar 298. A first valve peak 300 is also defined by the distal end of the first valve body 285 and is centered between the first valve collar supports 292. The peak 300 is a flow diverter. The first valve flues 294 allow fluid to flow therethrough and are provided to allow fluid to flow between the proximal end of the first valve body 285 and a lumen in the first valve collar 298.

Similarly, the female fitting shut-off valve 286 is constructed primarily of a second valve body 287 and a second spring 289. The second valve body 287 is positioned toward the proximal end of the female shaft 206. The proximal end of the second spring 289 is connected with the distal end of the second valve body 287 while the distal end of the second spring 289 is connected with a second cap 303 that fixedly interfaces with the distal end of the female shaft 206 to provide a stationary anchor for the second spring 289. The second cap 303 also tapers distally to form a second fluid port 305 extending into a lumen defined by the first tubing coupling 244. Rather than being integrally formed with the female fitting 204, in this embodiment the second cap 303 may be directly attached to the female shaft 206 or it may be sandwiched between the first tubing coupling 244 and the female shaft 206. In the latter case, the second cap 303 may be either snap-fitted or over-molded about the distal end of the female shaft 206, to allow for the prior insertion of the second shut-off valve 286 during assembly of the female fitting 204.

The proximal end of the female fitting lumen 207 in the female shaft 206 tapers slightly to reduce the diameter of the lumen 207 at the proximal end of the female shaft 206. The diameter of the second valve body 287 is slightly smaller than the diameter of the lumen 207 proximal from the female tapered portion 297. The distal end of the second valve body 287 is also encompassed by a second valve O-ring 291, which is slightly smaller in diameter than the lumen 207 distal to the female tapered portion 297. The proximal end of the second valve body 287 defines second valve flues 295 separated by second valve collar supports 293, which support a second valve collar 299. A second valve peak 301 is also defined by the proximal end of the second valve body 287 and is centered between the second valve collar supports 293. The peak 301 is a flow diverter. The second valve flues 295 allow fluid to flow therethrough and are provided to allow fluid to flow between the distal end of the second valve body 287 and a lumen in the second valve collar 299. (See arrow 307 for path of fluid through assembly).

Referring to FIG. 26, when the male fitting 202 is disengaged from the female fitting 204, the first spring 288 forces the first valve body 285 to move distally within the lumen 223 of the male shaft 222. The distal end of the first valve body 285, primarily the first valve collar 298, extends distally out of the lumen 223 past the distal end of the male shaft 222. The distal movement of the first valve body 285 is halted by the engagement of the first valve O-ring 290 with the male tapered portion 296. This engagement creates a fluid-tight seal between the first shut-off valve 284 and the male shaft 222 preventing fluid leakage from a tubing section connected with the second tubing coupling 254 on the male fitting 202.

Similarly, when the female fitting 204 is disengaged from the male fitting 202, the second spring 289 forces the second valve body 287 to move proximally within the lumen 207 of the female shaft 206. The proximal end of the second valve body 285, primarily the second valve collar 299, extends proximally out of the lumen 207 past the proximal end of the female shaft 206. The proximal movement of the second valve body 287 is halted by the engagement of the second valve O-ring 291 with the female tapered portion 297. This engagement creates a fluid-tight seal between the second shut-off valve 286 and the female shaft 206 preventing fluid leakage from a tubing section connected with the first tubing coupling 244 on the female fitting 204.

As shown in FIG. 25, when the male fitting 202 and the female fitting 204 are connected with each other, the first valve collar 298 and the second valve collar 299 interface. The first valve body 285 is thereby forced proximally within the male shaft 222 and the first valve O-ring 290 disengages from the male tapered portion 296 allowing fluid to flow past the first valve body 285, through the first valve flues 294, between the first valve collar supports 292, and out the lumen defined by the first valve collar 298. Likewise, the second valve body 287 is thereby forced distally within the female shaft 206 and the second valve O-ring 290 disengages from the female tapered portion 297 allowing fluid to flow past the second valve body 287, through the second valve flues 295, between the second valve collar supports 293, and out the lumen defined by the second valve collar 299. In this manner, the male fitting 202 can be connected with the female fitting 204 and automatically instantiate fluid flow through the connection assembly 201. Note that interaction between the clasps 12 and catches 8 are substantially the same as described above.

Figure 27:
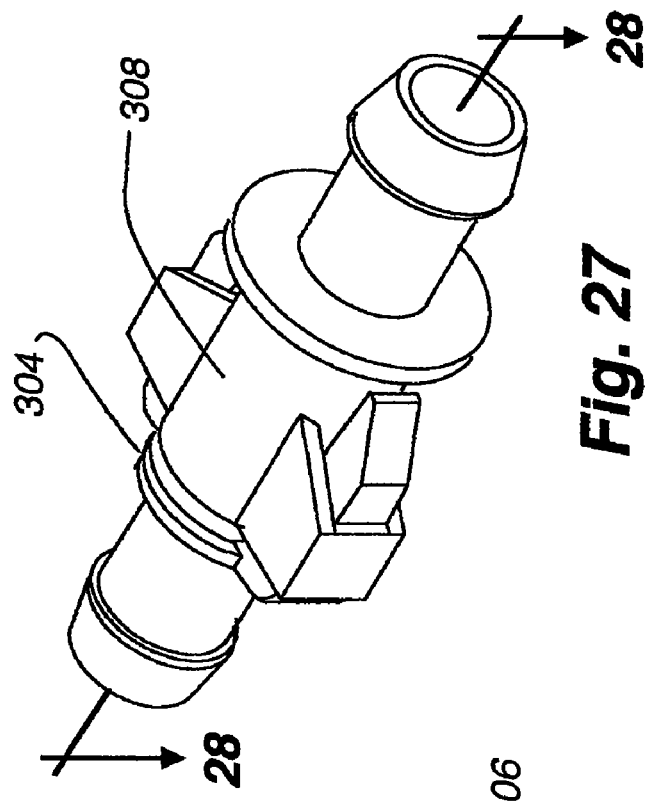
FIG. 27 is a perspective view of a connector having a face seal structure.
Figure 28:
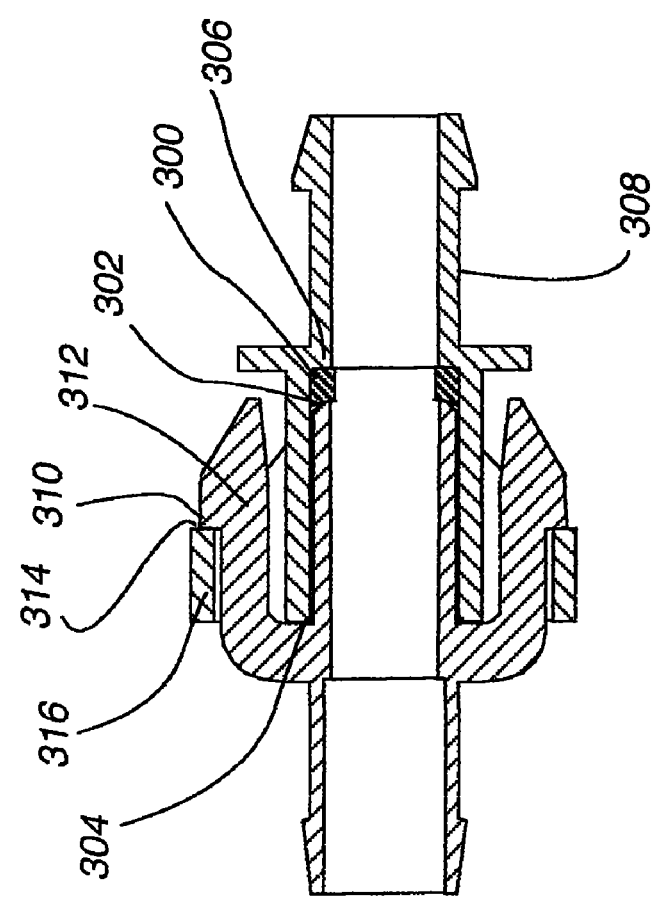
FIG. 28 is a cross-sectional view of the face seal member as indicated in FIG. 27.

FIGS. 27 and 28 show another embodiment of the present invention where a connector structure having a face seal, instead of a circumferential O-ring seal, between the male and female portions is used. A seal member 300, preferably an O-shape such as an O-ring or an O-ring having a square or rectangular cross section, is pinched or compressed between the terminal end 302 of the male fitting 304 and the internal base region 306 of the female fitting 308 when the male 304 and female fittings 308 are connected together. The retention shelf 310 on the tang 312 and the retention surface 314 on the catch 316 are designed to engage so that the space between the terminal end 302 of the male fitting 304 and the internal base region 306 of the female fitting 308 is less than the thickness of the face seal member 300. This dimensional conflict causes the terminal end 302 of the male fitting 304 to compress the face seal against the internal base region 306 of the female fitting 308, thereby creating a face seal, instead of a circumferential seal as is formed with an o-ring. The face seal member 300 may have an outer dimension sufficient to retain the face seal member within the female fitting when not held in place by the terminal end 302 of the male fitting. Both a circumferential seal and a face seal may be combined if desired. Note that structures not discussed as shown in previous embodiments and are left off to maximize detail of the present embodiment.

Figure 29:
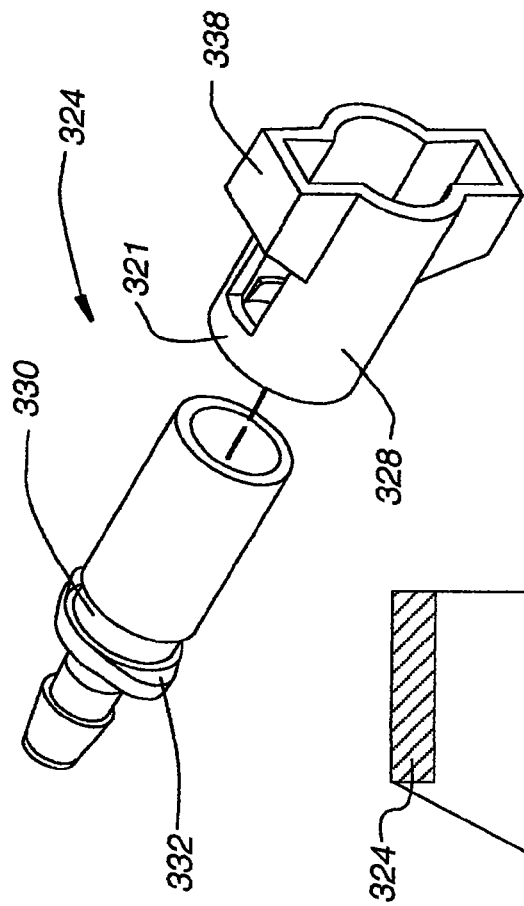
FIG. 29 is a perspective view of a connector having a rotating collar for receiving a male fitting.
Figure 30:
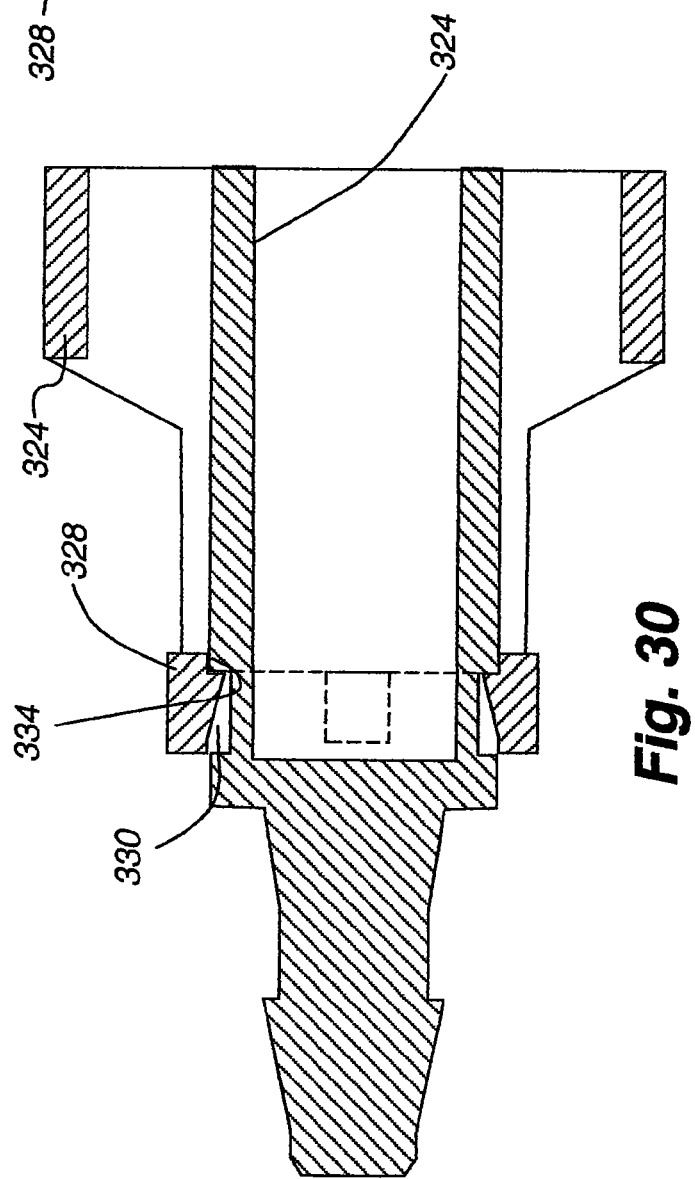
FIG. 30 is a cross-sectional view of the rotating collar embodiment as indicated in FIG. 29.

FIGS. 29 and 30 show a connection structure 320 of the present invention where the male (not shown) and female 321 portions can rotate relative to one another when in the engaged position. A catch structure 324 in this embodiment is formed with a collar 328, which fits over and is rotatably connected to the female connector portion 324. The female portion 324 of the connector 320 defines an annular groove 330 near the oblong grip flange 332. The collar 328 defines at least one protrusion 334 extending radially inwardly at the end of the collar 328 that overlaps the annular groove 330 when the collar is positioned on the female portion 324. The protrusion 334 extends into the annular groove 330 to keep the collar axially positioned on the female portion while allowing it to rotate therearound. The at least one protrusion can extend for a length at least partially circumferentially around the inside of the collar; there may be more than one such protrusion. Each protrusion may have a ramp, or sloped, shape to facilitate pushing the collar over the female portion more easily, but still sufficiently retaining the collar on the female portion.

When the male portion (not shown) is connected to the female portion 324, the tangs fit into and engage the catch 338 to hold the two pieces together. The two pieces may then rotate with respect to one another while maintaining engagement. When rotated, the tangs 336 cause the collar 328 to rotate around the female portion 324.

FIGS. 31 and 32 show a structure 338 that allows rotation of the male 340 and female 342 portions of the connection structure 338 relative to one another. In this embodiment, a catch 344 is formed as a circumferential collar 346 spaced around the female portion 346 by at least one rib 348. More than one rib 348 may be used, but the amount of rotation allowed would be reduced. The male portion 340 and the tangs 350 can rotate while engaged with the collar 346 to the point of contacting one of the support ribs 348 that supports and spaces the collar 346 around the female portion 342. The collar 346 may also be formed as a shroud attached at the end away from the male portion, with a slot formed circumferentially therein to allow the tangs and the male portion to rotate relative to the female portion (not shown). In this embodiment, the rotation would be limited by the ends of the groove formed in the collar.

Figure 33:
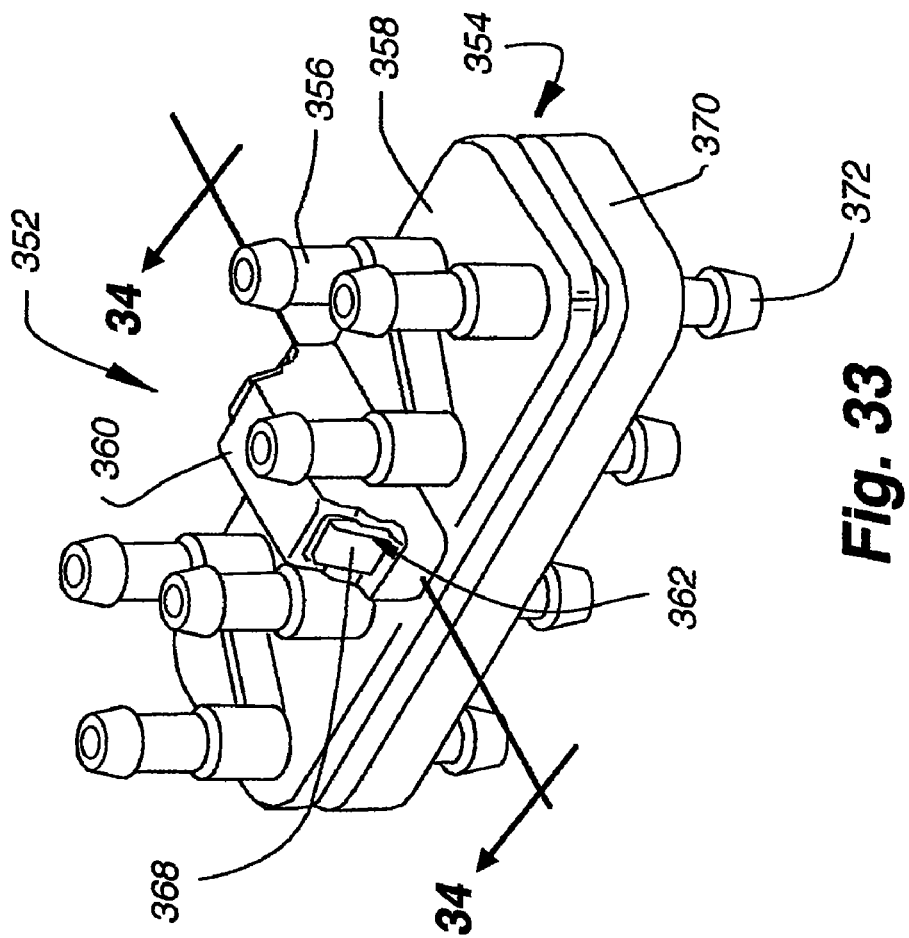
FIG. 33 is a perspective view of a multi-port assembly connected together using the buckle type structure of the present invention.
Figure 34:
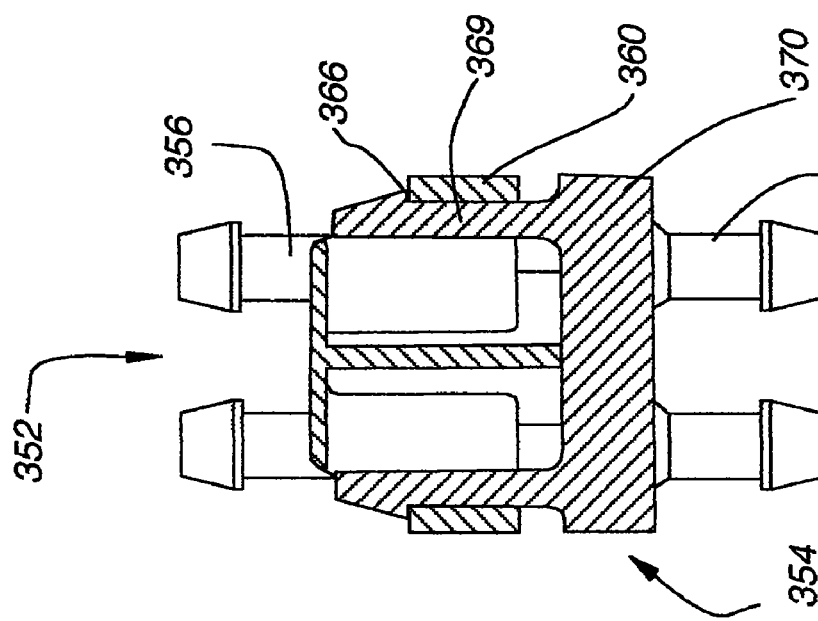
FIG. 34 is a cross-sectional view of the buckle type structure embodiment as indicated in FIG. 33.

FIGS. 33 and 34 show another embodiment of the present invention, where a gang of tube connectors 352 are held in engagement by a buckle structure 354. In FIG. 33, 6 female connector portions 356 are formed in a plate 358, three on each side of the catch structure 360. The catch structure 360 includes two clasp slots 362, each for receiving the clasp tab 364 and retention shelf 366 formed on each tang 368. The lower plate 370 forms six corresponding male connector portions 372 for receipt in respective female portions 356. As the male portions 372 are received in the respective female portions 356, the tangs 368 enter the catch structure 360 and insert through the clasp slots 362, respectively, to engage the catch structure 360 and retain the male portions 372 in connection with the female portions 356. In this embodiment, the tangs 368 extend from the plate 370 with the male portions 372, and the catch structure 360 is on the plate 374 with the female portions 356. This could be reversed if desired.

Any number of connection structure portions 356, 372 could be held in engagement by this embodiment, and more than one buckle structure 354 could be used to sufficiently hold the plates 370, 374 together, and thus the respective connector portions together. The male and female connector portions 356, 372 may be arranged to allow only one orientation of engagement between the gang of female connector portions and male connector portions. The catch 360 and tangs 368 are shown designed to engage near the periphery of the upper plate 374, which allows more convenient grasping by the user. The catch 360 and tangs 368 may also be designed to engage at a location away from the periphery if so desired.

Figure 35:
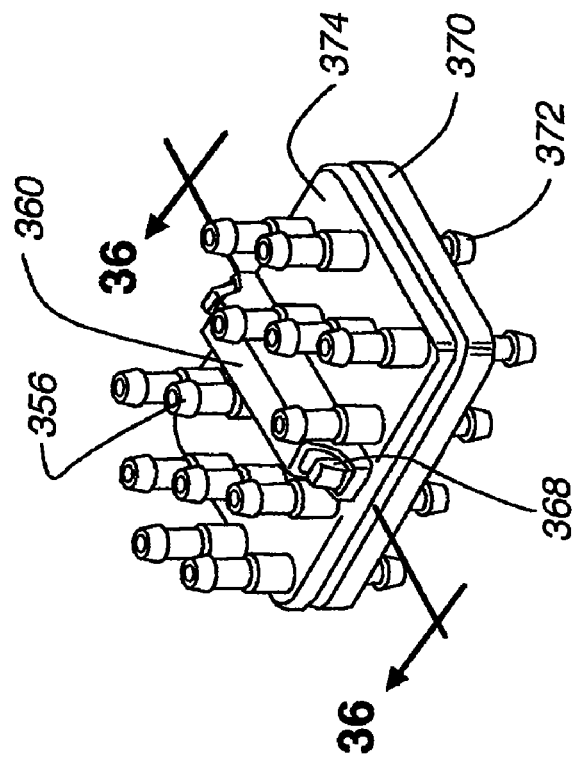
FIG. 35 is a perspective view of a multi-port assembly connected together using another buckle type structure of the present invention.
Figure 36:
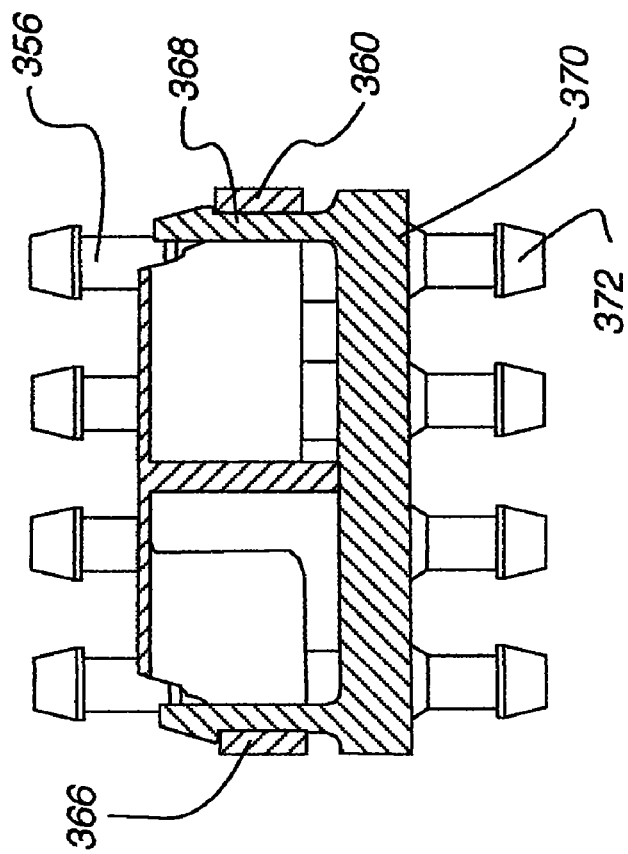
FIG. 36 is a cross-sectional view of the buckle type structure embodiment as indicated in FIG. 35.

FIGS. 35 and 36 show a gang of 10 female connector portions 356 on the upper plate 374 and 10 male connector portions 372 on the lower plate 370. The connection structure is similar to that shown in FIGS. 33 and 34. Note also that other numbers of female and male portions may be included in the gang, dependent on the plate size and needs or the user.

Figure 38:
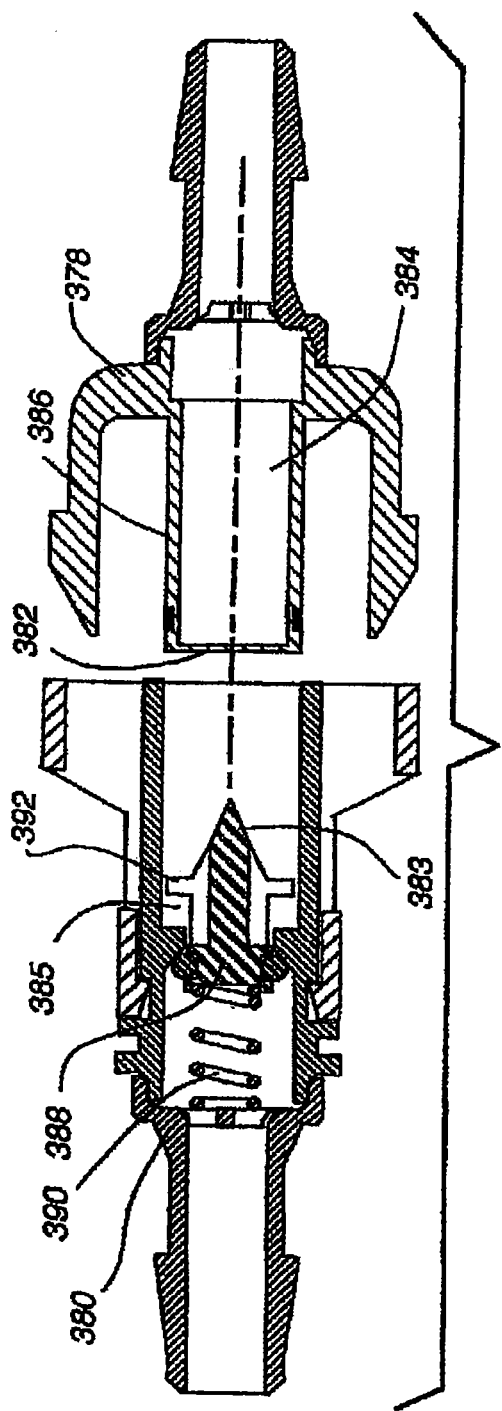
FIG. 38 is a representative embodiment of a disconnected male and female member showing the sharp member of the invention used for piercing a lumen seal.
Figure 37:
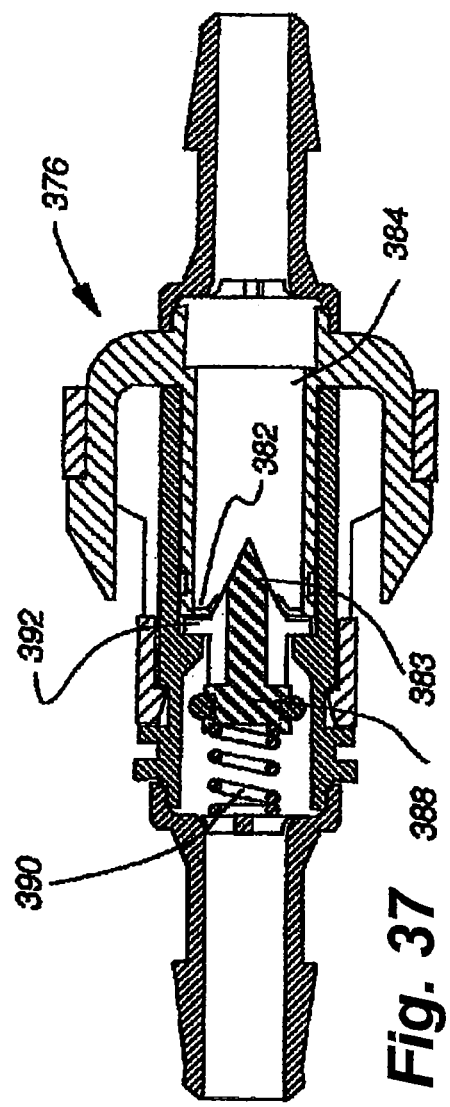
FIG. 37 shows a piercing structure embodiment formed inside the connecting structure of the present invention.

In another embodiment as shown in FIGS. 37 and 38, the connection structure 376 of the present invention allows piercing, when the two portions are connected, of a seal 382 formed either on the male 378 or female 380 connector portion. A tape seal or the like seal is formed over the female portion to preclude flow of a liquid therethrough, and the tape seal is punctured by a sharp 383 when the male portion 378 is inserted in to the female portion 380.

As shown in FIG. 37, the female portion 380 has a sharp 383 formed therein that extends into and through the lumen 384 of the male shaft 386. The extension of the sharp 383 into the lumen 384 pierces any type of seal 382 formed over the lumen 384, whether it be a tape seal, a plastic seal, or other type of diaphragm structure sealing the end of the lumen.

FIG. 38 shows the sharp 383 as a pointed structure formed within the channel inside the female connector portion 380. The sharp 383 may be fixed within the female portion, and used to puncture the seal 382 over the lumen of the male shaft upon connection of the male and female connector portions. The female portion would then be open at all times.

The sharp 383 can also be movably positioned in the channel 385 of the female portion 380. This allows the base 388 of the sharp member 383 to seal the channel of the female portion when not connected to a male portion. The sharp member 383 is biased into the sealed position by a spring 390. When connected with the male connector portion 378 and the male shaft 386 is inserted, the end of the sharp member 383 punctures the seal 382 on the lumen 384 of the male shaft 386, and the terminal end of the male shaft pushes on a collar or flange 392 formed near the sharp end 394 of the sharp member 383 to push the sharp out of a sealed engagement in the female end, opening up flow.

FIG. 37 further shows the sharp member 383 piercing the seal 382, and prior to the terminal end of the male shaft pushing the sharp member rearwardly. The fluid flows around or through particular portions of the sharp member 383. As contemplated herein, the sharp member 383 can be needle-like, or have a pyramidal shape with a pointed top, or can be simply sufficiently shaped to puncture the seal layer over the lumen. While shown here with the piercing sharp positioned in the female connector portion, with some structural modification the piercing sharp could also be in the male portion, having the same function described above.

As used herein, lumen refers not only to its definition, but also refers to an opening, aperture, or other passageway. The fluid referred to herein can be gaseous, liquid, or other state of material that is flowable through a tube (i.e. granular). The connector structures described above can be used with one clasp and one catch, or multiple clasps and catches. While generally described above as sealed when connected together, the connector structures may be sealed or unsealed.

The connection between the male and female connector portions and their respective tube sections can be by means other than a barbed fitting, such as, but not limited to threaded, press-fit without a barb, John Guest fitting, ferrule, and panel mount.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A connection assembly comprising:
a female portion comprising a female shaft defining a lumen and a plurality of catches disposed about the female shaft;
a male portion comprising a male shaft with an outside diameter that is less than an inner diameter of the lumen of the female shaft, and further defining an annular recess within an outer surface of the male shaft; and
a clasp assembly comprising a plurality of annularly disposed detents with tapered edges and a plurality of annularly disposed tangs with tapered edges, the detent and tangs being oriented coaxially with respect to each other, the tapered edges of the detents and the tapered edges of the tangs being orientated in radially opposite directions and being orientated in axially opposite directions, the detents and the tangs extending in radially opposite directions and extending in axially opposite directions; wherein
the detents seat into the annular recess to constrainedly couple the clasp assembly to the male portion, thereby constraining axial movement while allowing free rotation of the clasp assembly with respect to the male portion; the female portion and the male portion are releasably coupled to each other when the plurality of tangs seat into the plurality of catches; and
the clasp assembly remains coupled to the male portion when the male portion and the female portion are released from each other.

2. The connection assembly of claim 1, wherein the female portion, the male portion, and the clasp assembly are three separate pieces.

3. The connection assembly of claim 1, wherein the female shaft further comprises a finger grip flange having a first portion of its diameter the same as an outside diameter of the female shaft and a second portion of its diameter larger than the outside diameter of the female shaft.

4. The connection assembly of claim 3, wherein the catches are oriented substantially orthogonal to the finger grip flange.

5. The connection assembly of claim 3, wherein the male shaft further comprises an annular tab stop adjacent to the annular recess thereby stopping longitudinal movement of the female portion with respect to the male portion.

6. The connection assembly of claim 1, wherein a total number of detents in the plurality of detents exceeds a total number of tangs in the plurality of tangs.

7. The connection assembly of claim 1, wherein an interface between the male shaft and the female shaft forms a fluid-tight seal.

* * * * *